(12) United States Patent
Maciag et al.

(10) Patent No.: US 9,205,091 B2
(45) Date of Patent: Dec. 8, 2015

(54) DIAZENIUMDIOLATED COMPOUNDS, PHARMACEUTICAL COMPOSITIONS, AND METHOD OF TREATING CANCER

(75) Inventors: Anna E. Maciag, Frederick, MD (US); Larry K. Keefer, Bethesda, MD (US); Joseph E. Saavedra, Thurmont, MD (US); Lucy M. Anderson, Catonsville, MD (US); Harinath Chakrapani, Pashan Pune (IN)

(73) Assignee: The United States of America, as represented by the Secretary Department of Health and Human Services, Washington, DC (US)

( * ) Notice: Subject to any disclaimer, the term of this patent is extended or adjusted under 35 U.S.C. 154(b) by 486 days.

(21) Appl. No.: 13/509,431

(22) PCT Filed: Nov. 12, 2010

(86) PCT No.: PCT/US2010/056446
§ 371 (c)(1),
(2), (4) Date: Jun. 1, 2012

(87) PCT Pub. No.: WO2011/060215
PCT Pub. Date: May 19, 2011

(65) Prior Publication Data
US 2012/0238518 A1    Sep. 20, 2012

Related U.S. Application Data

(60) Provisional application No. 61/261,175, filed on Nov. 13, 2009.

(51) Int. Cl.
| | | |
|---|---|---|
| A61K 31/4965 | (2006.01) | |
| C07D 241/04 | (2006.01) | |
| C07D 295/32 | (2006.01) | |
| A61K 31/551 | (2006.01) | |

(52) U.S. Cl.
CPC ........... *A61K 31/551* (2013.01); *A61K 31/4965* (2013.01)

(58) Field of Classification Search
CPC . A61K 31/4965; C07D 241/04; C07D 295/32
USPC ...................................... 514/255.01; 544/382
See application file for complete search history.

(56) References Cited

U.S. PATENT DOCUMENTS

| | | | |
|---|---|---|---|
| 6,610,660 B1 | 8/2003 | Saavedra et al. | |
| 6,911,433 B2 | 6/2005 | Saavedra et al. | |
| 7,081,524 B2 | 7/2006 | Saavedra et al. | |
| 7,332,590 B2 | 2/2008 | Nacht et al. | |
| 2008/0096235 A1 | 4/2008 | Kimberly et al. | |
| 2014/0315865 A1* | 10/2014 | Maciag et al. | 514/150 |

FOREIGN PATENT DOCUMENTS

| | | |
|---|---|---|
| WO | WO 98/13358 A1 | 4/1998 |
| WO | WO 03/080039 A1 | 10/2003 |
| WO | WO 2007/127725 A2 | 11/2007 |
| WO | WO 2009/114368 A2 | 9/2009 |

OTHER PUBLICATIONS

Liou et al., Reactive Oxygen Species in Cancer, Free Radic Res., vol. 44, No. 5, pp. 1-31, May 2010.*
Chakrapani et al., "Synthesis, mechanistic studies, and anti-proliferative activity of glutathione/glutathione S-transferase-activated nitric oxide prodrugs," *Bioorganic &Medicinal Chemistry*, 16 (22), 9764-9771 (2008).
Denlinger et al., "Proteasome inhibition sensitizes non-small cell lung cancer to histone deacetylase inhibitor-induced apoptosis through the generation of reactive oxygen species," *J. Thorac. Cardiovasc. Surg.*, 128 (5), 740-748 (2004).
International Search Report, Application No. PCT/US2010/056446, dated Feb. 14 2011.
Kiziltepe et al., "JS-K, a GST-activated nitric oxide generator, induces DNA double-strand breaks, activates DNA damage response pathways, and induces apoptosis in vitro and in vivo in human multiple myeloma cells," *Blood*, 110 (2), 709-718 (2007).
Ling et al., "Reactive oxygen species generation and mitochondrial dysfunction in the apoptotic response to Bortezomib, a novel proteasome inhibitor, in human H460 non-small cell lung cancer cells," *J. Biol. Chem.*, 278 (36), 33714-33723 (2003).
Liu et al., "Nitric oxide prodrugs and metallochemotherapeutics: JS-K and CB-3-100 enhance arsenic and cisplatin cytolethality by increasing cellular accumulation," *Mol. Cancer Ther.*, 3 (6), 709-714 (2004).

(Continued)

*Primary Examiner* — Brenda Coleman
(74) *Attorney, Agent, or Firm* — Leydig, Voit & Mayer

(57) ABSTRACT

Disclosed is a method of treating cancer in a patient comprising administering to the patient an effective amount of a diazeniumdiolated ($N_2O_2$-containing) compound or a pharmaceutically acceptable salt thereof, wherein the cancer cell has an elevated level of reactive oxygen species (ROS) and/or a decreased level of one or more of PRX1, PRX6, and OGG1, compared to a normal cell of the same tissue or tissue type. An example of a diazeniumdiolated compound is Formula (I), wherein X and Q are defined herein. Also disclosed are diazeniumdiolated compounds, pharmaceutical compositions, and methods of use including enhancing the chemotherapeutic treatment of chemotherapeutic agents and high energy radiation.

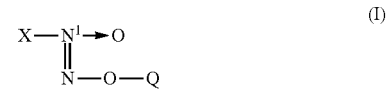

31 Claims, 5 Drawing Sheets

(56) References Cited

OTHER PUBLICATIONS

Figure 2:
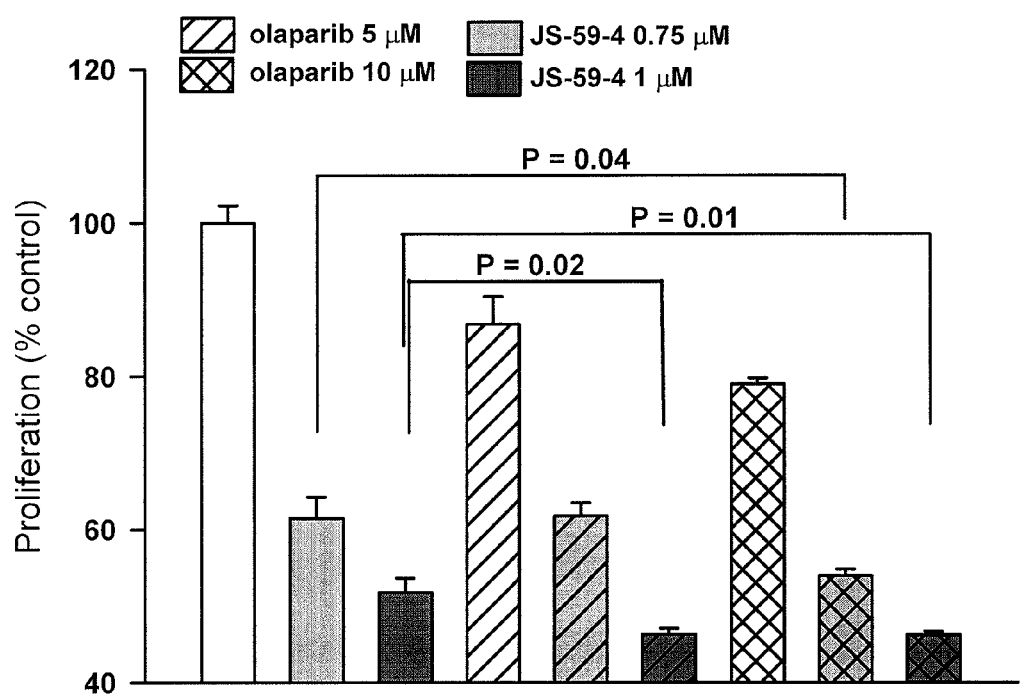

Lu et al., "Models of reactive oxygen species in cancer," *Drug Discov. Today Dis. Models*, 4 (2), 67-73 (2007).

Maciag et al., "The nitric oxide prodrug JS-K and its structural analogues as cancer therapeutic agents," *Anticancer Agents Med. Chem.*, 9 (7), 798-803 (2009).

Maciag et al., "The nitric oxide prodrug JS-K is effective against non-small-cell lung cancer cells in vitro and in vivo: involvement of reactive oxygen species," *J. Pharmacol. Exp. Ther.*, 336 (2), 313-320 (2010).

Nandurdikar et al., "Synthesis and evaluation of piperazine and homopiperazine analogues of JS-K, an anti-cancer lead compound," *Bioorg. Med. Chem. Lett.*, 19 (10), 2760-2762 (2009).

Romanowska et al., "DNA damage, superoxide, and mutant K-ras in human lung adenocarcinoma cells," *Free Radic. Biol. Med.*, 43 (8), 1145-1155 (2007).

Saavedra et al., "The secondary amine/nitric oxide complex ion $R_2N[N(O)NO]$ as nucleophile and leaving group in $S_NAr$ reactions," *J. Org. Chem.*, 66 (9), 3090-3098 (2001).

Shami et al., "Antitumor activity of JS-K [$O^2$-(2,4-dinitrophenyl) 1-[(4-Ethoxycarbonyl)piperazin-1-yl]diazen-1-ium-1,2-diolate] and related $O^2$-aryl diazeniumdiolates in vitro and in vivo," *J. Med. Chem.*, 49 (14), 4356-4366 (2006).

Shami et al., "JS-K, a glutathione/glutathione S-transferase-activated nitric oxide donor of the diazeniumdiolate class with potent antineoplastic activity," *Mol. Cancer Ther.*, 2 (4), 409-417 (2003).

Waris et al., "Reactive oxygen species: role in the development of cancer and various chronic conditions," *J. Carcinog.*, 5 (14), 1-8 (2006).

Zanke et al., "The stress-activated protein kinase pathway mediates cell death following injury induced by *cis*-platinum, UV irradiation or heat," *Curr. Biol.*, 6 (5), 606-613 (1996).

\* cited by examiner

FIGURE 1A
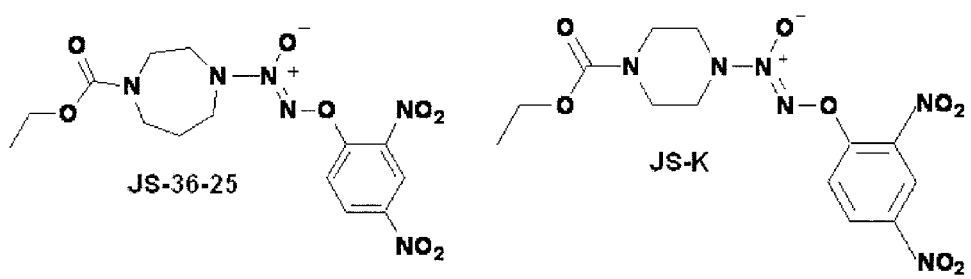
FIGURE 1B
| Cell line | IC$_{50}$ (µM) |
|---|---|
| H441 | 0.81 |
| A549 | 2.60 |
| H838 | 5.11 |
| H1693 | 0.80 |
| H1703 | 0.45 |
| H1734 | 0.40 |
| H1944 | 3.58 |
| H2126 | 3.60 |
FIGURE 1C
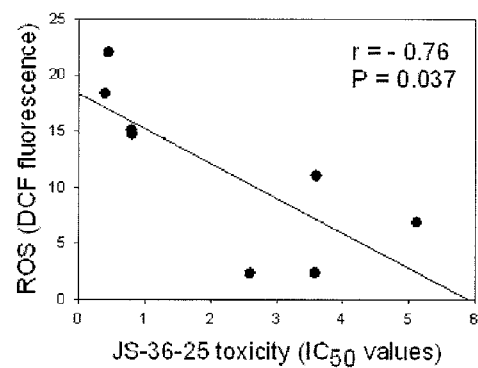

H1703 control

H1703; 1 µM JS-36-25, 60 min

H1703; 1 µM JS-36-25, 4 hours

DIAZENIUMDIOLATED COMPOUNDS, PHARMACEUTICAL COMPOSITIONS, AND METHOD OF TREATING CANCER

CROSS-REFERENCE TO A RELATED APPLICATION

This application is a U.S. national phase of International Patent Application No. PCT/US10/56446, filed Nov. 12, 2010, which claims the benefit of U.S. Provisional Patent Application No. 61/261,175, filed Nov. 13, 2009, the disclosures of which are incorporated by reference.

BACKGROUND OF THE INVENTION

Cancer is a major health problem worldwide. Particularly, lung cancer is the leading cause of cancer deaths worldwide. Non-small cell lung cancer (NSCLC) accounts for about 80% of all lung cancers. Despite the recent advantages of therapies, the disease is rarely curable, with poor prognosis and overall 5-year survival rate of only 15%. With current platinum-based chemotherapy regimens, medial survival is 7-10 months. Progress in understanding of the cancer biology and mechanisms of oncogenesis has allowed the development of several potential molecular targets for NSCLC treatment. Several targeted agents have been introduced in clinical trials in NSCLC. The main agents that have been investigated are epidermal growth factor receptor (EGFR), tyrosine kinase family inhibitors (TKIs), angiogenesis inhibitors, and various signal transduction inhibitors. EGFR-TKIs, such as gefitinib and erlotinib, are active as single agents only in small subsets of patients with specific biological and/or pathological features. There exists an unmet need for agents suitable for treating cancers, particularly heterogeneous cancers such as lung cancer.

BRIEF SUMMARY OF THE INVENTION

The invention provides a method of treating cancer in a patient comprising administering to the patient an effective amount of a diazeniumdiolated ($N_2O_2$-containing) compound or a pharmaceutically acceptable salt thereof, wherein the cancer cell has an elevated level of reactive oxygen species (ROS), and/or a decreased level of one or more of PRX1, PRX6, and OGG1, compared to a normal cell of the same tissue or tissue type. For example, in one aspect, the method is applicable to treating cancers wherein the cancer cell has an elevated ROS content which is reflected by low levels of antioxidant enzymes.

Accordingly, the invention provides a method as described above, wherein the diazeniumdiolated compound is a compound of the formula (I):

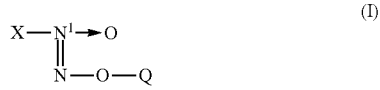

wherein
X is selected from the group consisting of amino, alkylamino, dialkylamino, arylamino, diarylamino, a polyamino, alkyl, alkenyl, alkynyl, aryl, heteroaryl, and heterocyclyl, which are optionally substituted, and Q comprises an aryl, heteroaryl, or heterocyclyl group, which are optionally substituted.

The present invention further provides a compound of the formula:

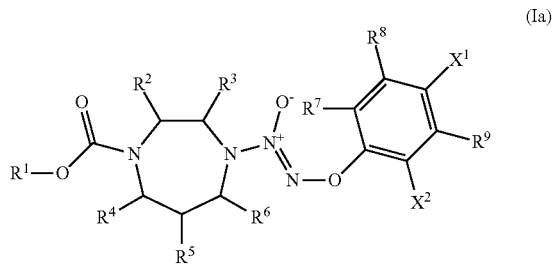

wherein $R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and $R^2$ to $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;

$X^1$ and $X^2$ are independently nitro or cyano;

or a pharmaceutically acceptable salt thereof;

with the proviso that when all of $R^2$ to $R^9$ are H and $X^1$ and $X^2$ are both nitro, then $R^1$ is not an unsubstituted alkyl group.

The invention also provides pharmaceutical compositions and method of treating cancer by the use of the above compounds. The invention further provides a method for enhancing the chemotherapeutic treatment of cancer or radiation treatment of cancer.

BRIEF DESCRIPTION OF THE SEVERAL VIEWS OF THE DRAWING(S)

FIG. 1A shows a comparison of the structures of $O^2$-(2,4-dinitrophenyl) 1-[(4-ethoxycarbonyl)homopiperazin-1-yl]diazen-1-ium-1,2-diolate ("JS-36-25") and JS-K. FIG. 1B illustrates $IC_{50}$ values obtained for NSCLC cells treated with JS-36-25 in an embodiment of the invention. FIG. 1C illustrates that the toxicity of JS-36-25 (as $IC_{50}$ values) correlates with endogenous ROS levels, measured as DCF fluorescence.

FIG. 2 is a bar graph showing a synergistic effect of the administration of JS-59-4 with the PARP inhibitor olaparib in the inhibition of proliferation of lung adenocarcinoma cells (cell line H441). The white bar represents the control (i.e., no treatment). The light gray bar represents the administration of JS-59-4 alone (0.75 μM). The dark gray bar represents the administration of JS-59-4 alone (1 μM). The diagonally hatched bar represents the administration of olaparib alone (5 μM). The cross hatched bar represents the administration of olaparib alone (10 μM). The light gray diagonally gray bar represents the co-administration of JS-59-4 (0.75 μM) and olaparib (5 μM). The dark gray diagonally hatched bar represents the co-administration of JS-59-4 (1 μM) and olaparib (5 μM). The light gray cross hatched gray bar represents the co-administration of JS-59-4 (0.75 μM) and olaparib (10

μM). The dark gray cross hatched bar represents the co-administration of JS-59-4 (1 μM) and olaparib (10 μM).

Figure 3A:
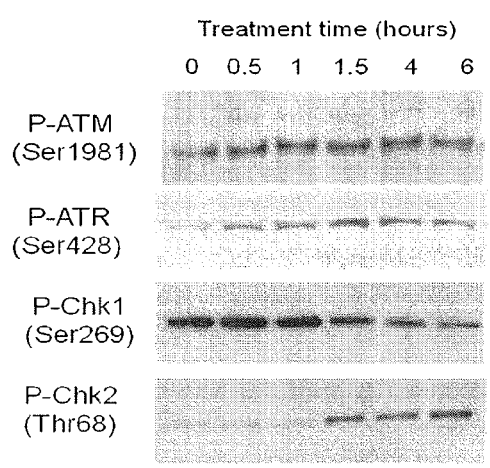
Figure 3B:
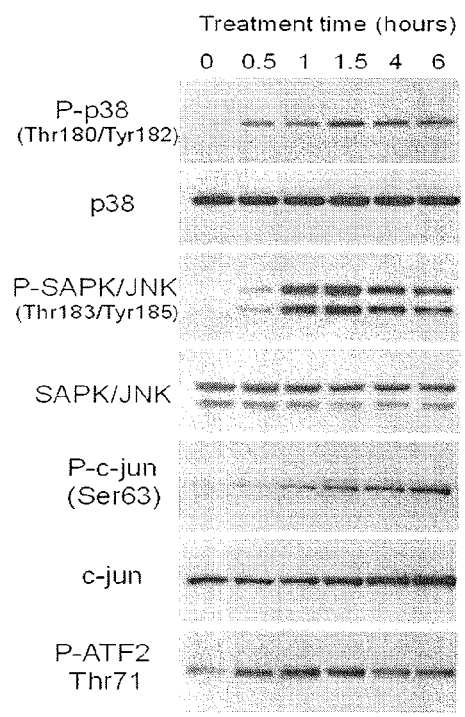
Figure 3C:
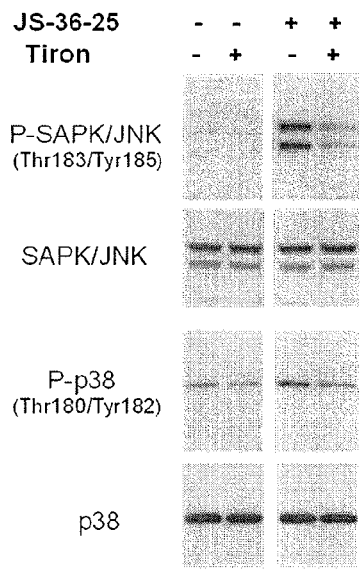
Figure 3D:
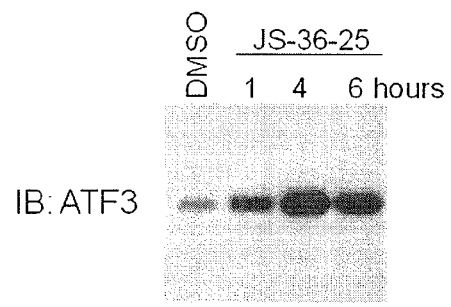

FIG. 3A depicts a Western blot analysis of ATM/ATR pathway activation upon JS-36-25 treatment in an embodiment of the invention. FIG. 3B illustrates that stress kinases p38 and SAPK/JNK are activated by phosphorylation. Total p38 and SAPK/JNK protein levels are shown as loading controls. FIG. 3C depicts pretreatment with ROS scavenger Tiron (10 mM, 1 h) attenuates SAPK/JNK and p38 activation, confirming the importance of ROS signaling in JS-36-25 toxicity. FIG. 3D illustrates that ATF3 protein is upregulated upon JS-36-25 treatment, as indicated by Western blot.

Figure 4A:
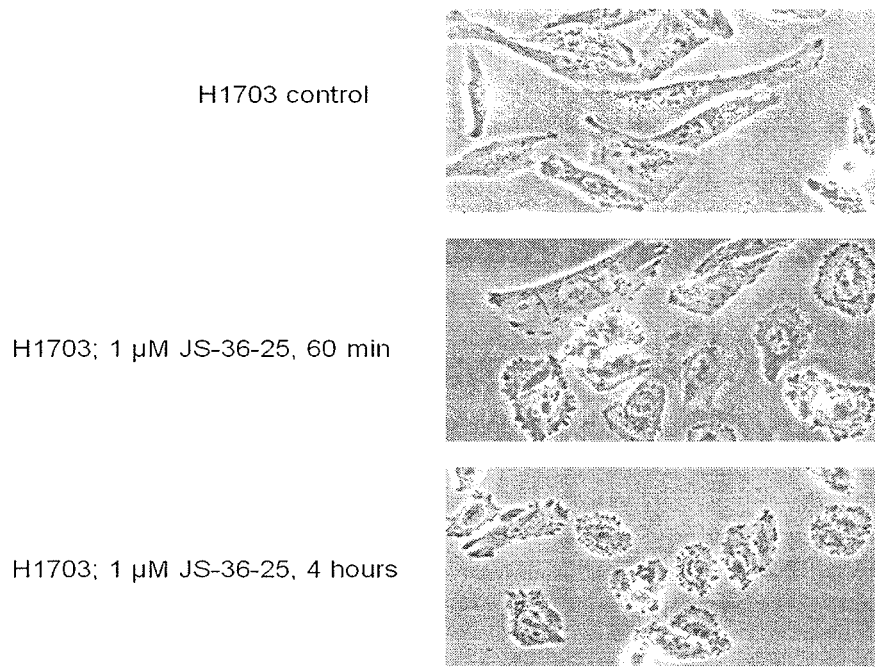
Figure 4B:
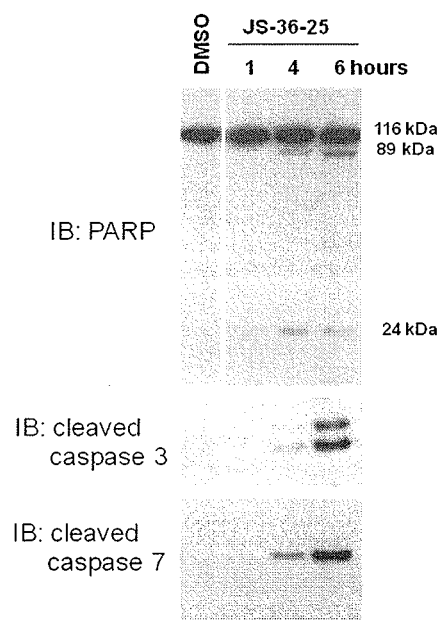

FIG. 4A illustrates that morphological changes (membrane blebbing) occur less than one hour after drug treatment is initiated with JS-36-25 in H1703 cells in an embodiment of the invention. FIG. 4B illustrates PARP cleavage and effector caspases 3 and 7 activation as shown by Western blot.

Figure 5A:
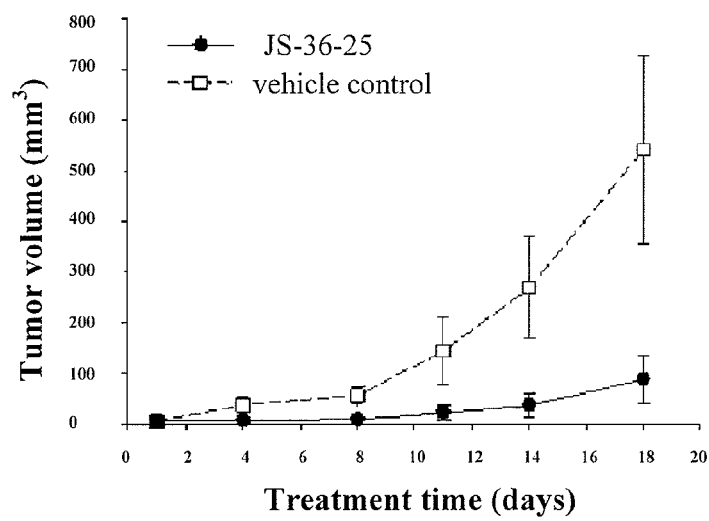
Figure 5B:
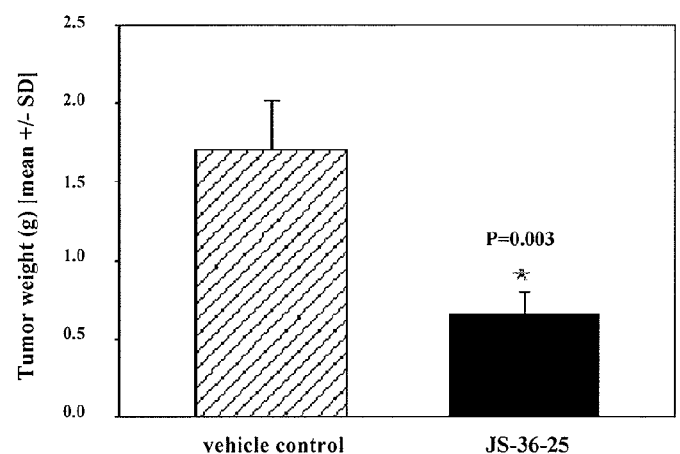
Figure 5C:
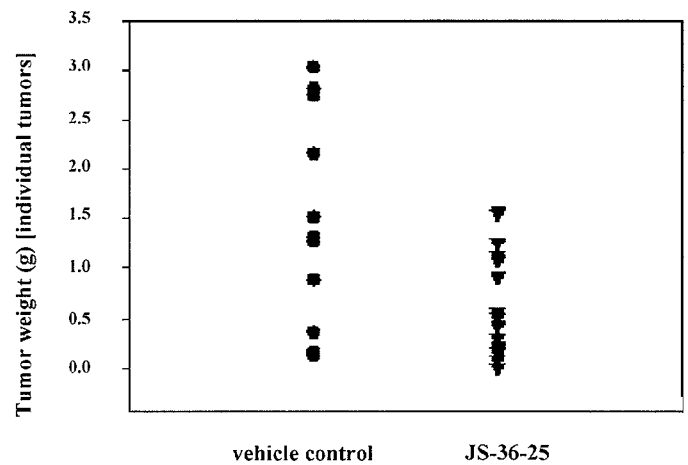

FIG. 5A illustrates that JS-36-25 reduces growth of NSCLC cells in vivo as JS-36-25 is administered I.V. at 6 μmoles/kg, three times a week in an embodiment of the invention. Tumors are measured with a caliper. FIGS. 5B and 5C depict that JS-36-25 treatment reduces tumors weight, as mean+/−SD (FIG. 5B) and as individual tumors (FIG. 5C).

DETAILED DESCRIPTION OF THE INVENTION

In accordance with an embodiment, the invention provides a method of treating cancer in a patient comprising administering to the patient an effective amount of a diazeniumdiolated ($N_2O_2$-containing) compound or a pharmaceutically acceptable salt thereof, wherein the cancer cell has an elevated level of reactive oxygen species (ROS) and/or a decreased level of one or more of PRX1, PRX6, and OGG1, compared to a normal cell of the same tissue or tissue type. For example, the method is applicable to treating cancers wherein the cancer cell has an elevated ROS content which is reflected by low levels of antioxidant enzymes. Alternatively or in addition, the method is applicable to treating cancers wherein the cancer cell has a decreased level of one or more of PRX1, PRX6, and OGG1 compared to a normal cell.

Suitable diazeniumdiolated ($N_2O_2$-containing) compounds include those described in U.S. Pat. Nos. 7,018,524, 6,610,660, and 6,911,433 and International Patent Applications WO 03/080039 A1 and WO 2009/114368 A1, the contents of which are incorporated by reference.

It is preferred that the diazeniumdiolated ($N_2O_2$-containing) compound for use in the method is compound of formula (I):

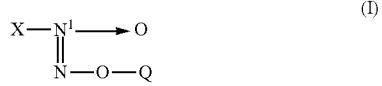

(I)

wherein

X is selected from the group consisting of amino, alkylamino, dialkylamino, arylamino, diarylamino, a polyamino, alkyl, alkenyl, alkynyl, aryl, heteroaryl, and heterocyclyl, and Q comprises an aryl, heteroaryl, or heterocyclyl group, wherein X and Q are optionally substituted.

Suitable groups for X include phenyl, biphenyl, naphthyl, anthracenyl, pyrenyl pyridinyl, pyridazinyl, pyrimidyl, pyrazinyl, benzimidazolyl, triazinyl, imidazolyl, (1,2,3)- and (1,2,4)-triazolyl, pyrazolyl, tetrazolyl, furyl, thienyl, isothiazolyl, thiazolyl, isoxazolyl, oxadiazolyl, isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl. In preferred embodiments, X is piperazinyl, homopiperazinyl, pyrrolyl, pyrrolinyl, pyrazolyl, pyranyl, piperidyl, or morpholinyl. Preferably, X is piperazinyl or homopiperazinyl.

Suitable groups for Q include acridinyl, anthracenyl, benzofuranyl, benzothiophenyl, benzoxazolyl, benzopyrazolyl, benzothiazolyl, carbazolyl, chlorophyllyl, cinnolinyl, furanyl, imidazolyl, indolyl, isobenzofuranyl, isoindolyl, isoxazolyl, isothiazolyl, isoquinolinyl, naphthalenyl, oxazolyl, phenyl, phenanthrenyl, phenanthridinyl, phenothiazinyl, phenoxazinyl, phthalimidyl, phthalazinyl, phthalocyaninyl, porphinyl, pteridinyl, purinyl, which is optionally part of a nucleic acid, ribosylpurinyl, pyrazinyl, pyrazolyl, pyridazinyl, pyridinyl, pyrimidinyl, which is optionally part of a nucleic acid, ribosylpyrimidinyl, pyrrocolinyl, pyrrolyl, quinolinyl, quinoxalinyl, quinazolinyl, tetrazolyl, thiazolyl, thiophenyl, thyroxinyl, triazinyl, an aryl-containing vitamin, an aryl-containing hormone, and triazolyl. In some embodiments, Q is phenyl, an aryl-containing vitamin, an aryl-containing hormone, a pyrimidinyl, which is optionally part of a nucleic acid, ribosylpyrimidinyl, purinyl, which is optionally part of a nucleic acid, or a ribosylpurinyl. Preferably, Q is phenyl that is optionally substituted.

X and Q are optionally substituted with one or more moieties (e.g., 1 to 5, 1 to 4, 1 to 3, 1 or 2) selected from the group consisting of —[N(NO)O⁻], halo, hydroxy, alkylthio, arylthio, alkoxy, aryloxy, amino, alkylamino, dialkylamino, nitroso, cyano, sulfonato, mercapto, nitro, oxo (═O), alkyl, alkenyl, cycloalkyl, heterocycloalkyl, arylalkyl, aryl, benzylcarbonyl, phenylcarbonyl, phosphono, and phosphato. Q can also be optionally substituted with X[N(O)NO]⁻, wherein X is as defined herein.

In certain embodiments, Q is substituted with at least one moiety selected from the group consisting of alkyl, alkoxy, nitro, and cyano. Preferably, Q is phenyl that is optionally substituted with at least one moiety selected from the group consisting of alkyl, alkoxy, nitro, and cyano (e.g., 2,4-dinitrophenyl, 2-cyano-4-nitrophenyl, 2-nitro-4-cyanophenyl, 2,4-dinitro-5-methylphenyl, 2,4-dinitro-5-methoxyphenyl, 2-cyano-4-nitro-5-methylphenyl, 2-cyano-4-nitro-5-methoxyphenyl, 2-nitro-4-cyano-5-methylphenyl, 2-nitro-4-cyano-5-methoxyphenyl. In certain preferred embodiments, when Q is any of the foregoing groups, X is preferably a heterocyclyl (e.g., piperazinyl, homopiperazinyl).

In a preferred embodiment, the compound of formula (I) is a compound of formula (Ia):

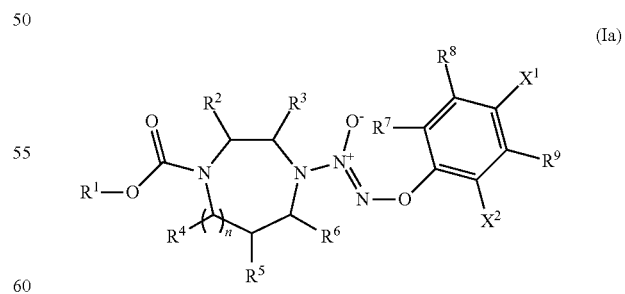

(Ia)

wherein $R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and $R^2$ to $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;

$X^1$ and $X^2$ are independently nitro or cyano;

n is 0 or 1.

In certain embodiments, $X^1$ and $X^2$ are both nitro in the compound of formula (Ia). In certain other embodiments, one of $X^1$ and $X^2$ is nitro and the other is cyano. In some other embodiments, $X^1$ and $X^2$ are both cyano.

In certain embodiments, n preferably is 1. Alternatively, n preferably is 0.

In any of the foregoing embodiments, $R^7$, $R^8$, and/or $R^9$ are the same or different and each is a moiety selected from the group consisting of H, alkyl, alkenyl, alkynyl, aryl alkyl, aryl, hydroxyalkyl, haloalkyl, aminoalkyl, alkoxy, aryloxy, and thioalkoxy in the compound of formula (Ia). Preferably, $R^8$ is alkyl or alkoxy.

The invention also provides a compound of the formula (Ib):

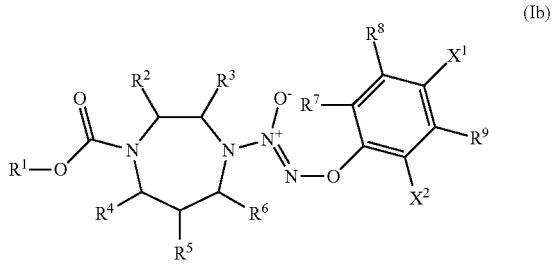

wherein $R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and $R^2$ to $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;

$X^1$ and $X^2$ are independently nitro or cyano;

or a pharmaceutically acceptable salt thereof;

with the proviso that when all of $R^2$ to $R^9$ are H and $X^1$ and $X^2$ are both nitro, then $R^1$ is not an unsubstituted alkyl group.

In certain embodiments, $X^1$ and $X^2$ are both nitro in the compound of formula (Ib). In other embodiments, one of $X^1$ and $X^2$ is nitro and the other is cyano. In some other embodiments, $X^1$ and $X^2$ are both cyano.

In any of the foregoing embodiments of the compound of formula (Ib), $R^7$, $R^8$, and/or $R^9$ are the same or different and each is a moiety selected from the group consisting of H, alkyl, alkenyl, alkynyl, aryl alkyl, aryl, hydroxyalkyl, haloalkyl, aminoalkyl, alkoxy, aryloxy, and thioalkoxy in the compound of formula (Ib). Preferably, $R^8$ is alkyl or alkoxy.

The invention also provides a compound of the formula (Ic):

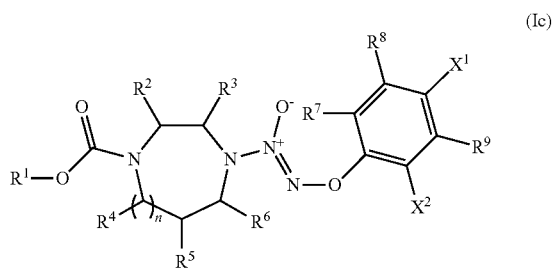

wherein $R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and $R^2$ to $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;

$X^1$ and $X^2$ are independently nitro or cyano;

wherein at least one of $X^1$ and $X^2$ is cyano;

n is 0 or 1;

or a pharmaceutically acceptable salt thereof.

In certain embodiments, $X^1$ and $X^2$ are both cyano in the compound of formula (Ic). In other embodiments, one of $X^1$ and $X^2$ is nitro and the other is cyano. In some other embodiments, $X^1$ and $X^2$ are both nitro.

In certain embodiments, n preferably is 1. Alternatively, n preferably is 0.

In any of the foregoing embodiments, $R^7$, $R^8$, and/or $R^9$ are the same or different and each is a moiety selected from the group consisting of H, alkyl, alkenyl, alkynyl, aryl alkyl, aryl, hydroxyalkyl, haloalkyl, aminoalkyl, alkoxy, aryloxy, and thioalkoxy in the compound of formula (Ic). Preferably, $R^8$ is alkyl or alkoxy.

The invention provides a pharmaceutical composition comprising a compound of formula (Ib), (Ic), or a salt thereof and a pharmaceutically acceptable carrier.

Further provided is a method of treating cancer in a patient (e.g., human) comprising administering an effective amount of a compound of formula (Ib), (Ic), or a salt thereof to the patient.

In accordance with an embodiment, the invention provides a method of treating cancer in a patient comprising administering to the patient an effective amount of a diazeniumdiolated ($N_2O_2$-containing) compound (e.g., a compound of formula (I) or (Ia)) or a pharmaceutically acceptable salt thereof, wherein the cancer cell has a peroxiredoxin 6 (PRX6) content less than about 10 units relative to the PRX6 content of a nonmalignant lung epithelial cell HPL1D which is 100 units.

The present invention also provides a method of enhancing chemotherapeutic treatment of cancer with a chemotherapeutic agent that produces reactive oxygen species (ROS) in the cancer cell or radiation treatment of cancer, the method comprising administering an effective amount of a compound of formula (I), (Ia), or a pharmaceutically acceptable salt thereof. The compound or salt of formula (I) or (Ia) can be administered simultaneously with the chemotherapeutic treatment or radiation treatment, sequentially with chemotherapeutic treatment or radiation treatment, or cyclically with chemotherapeutic treatment or radiation treatment. For example, the compound of formula (I) or (Ia) can be administered prior to the chemotherapeutic treatment or radiation treatment or the compound of formula (I) or (Ia) is administered subsequent to the chemotherapeutic treatment or radiation treatment.

In any of the embodiments above, the term "alkyl" implies a straight-chain or branched alkyl substituent containing from, for example, about 1 to about 12 carbon atoms, preferably from about 1 to about 8 carbon atoms, more preferably from about 1 to about 6 carbon atoms. In accordance with an embodiment, the alkyl group is preferably a $C_1$-$C_3$ alkyl. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs, such as in hydroxyalkyl, monohalo alkyl, dihalo alkyl, and trihalo alkyl.

In any of the embodiments above, the term "alkenyl," as used herein, means a linear alkenyl substituent containing from, for example, about 2 to about 12 carbon atoms (branched alkenyls are about 3 to about 12 carbons atoms), preferably from about 2 to about 8 carbon atoms (branched alkenyls are preferably from about 3 to about 8 carbon atoms), more preferably from about 3 to about 6 carbon atoms. In accordance with an embodiment, the alkenyl group is preferably a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like.

In any of the embodiments above, the term "alkynyl," as used herein, means a linear alkynyl substituent containing at least one carbon-carbon triple bond and from, for example, about 2 to about 12 carbon atoms (branched alkynyls are about 4 to about 12 carbons atoms), preferably from about 2 to about 8 carbon atoms (branched alkynyls are preferably from about 4 to about 8 carbon atoms), more preferably from about 3 to about 6 carbon atoms. Examples of such substituents include propynyl, propargyl, n-butynyl, pentynyl, isopentynyl, hexynyl, octynyl, dodecynyl, and the like.

In any of the embodiments above, the term "alkoxy" embraces linear or branched alkyl groups that are attached to divalent oxygen. The alkyl group is the same as described herein. In accordance with an embodiment, the alkoxy group is preferably a $C_1$-$C_3$ alkoxy. Examples of alkoxy group include methoxy, ethoxy, n-propoxy, isopropoxy, n-butoxy, sec-butoxy, isobutoxy, tert-butoxy, n-pentoxy, isopentoxy, n-hexoxy, and the like. The term "aryloxy" refers to substituents that have an aryl group attached to divalent oxygen. The aryl group is the same as described herein. Examples of such substituents include phenoxy.

In any of the embodiments above, the term "halo" refers to a halogen selected from the group consisting of fluorine, chlorine, bromine, and iodine, preferably chlorine or bromine.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2π electrons, according to Hückel's Rule, wherein n=1, 2, or 3.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, thienyl, isothiazolyl, thiazolyl, isoxazolyl, and oxadiazolyl.

In any of the embodiments above, the term "heterocyclyl" means a stable, saturated, or partially unsaturated monocyclic, bicyclic, and spiro ring system containing 3 to 7 ring members of carbon atoms and other atoms selected from nitrogen, sulfur, and/or oxygen. Preferably, a heterocyclyl is a 5, 6, or 7-membered monocyclic ring and contains one, two, or three heteroatoms selected from nitrogen, oxygen, and/or sulfur. The heterocyclyl may be attached to the parent structure through a carbon atom or through any heteroatom of the heterocyclyl that results in a stable structure. Examples of such heterocyclic rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl.

In any of the embodiments above, the term "aryl alkyl" as utilized herein means alkyl as defined herein, wherein at least one hydrogen atom is replaced with an aryl substituent as defined herein. Aryl alkyls include, for example, benzyl, phenethyl, and substituents of the formula:

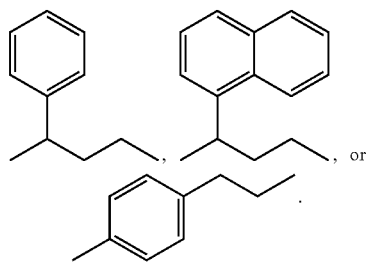

In any of the embodiments above, the term "alkylamino" refers to a secondary amine substituent with one hydrogen and one alkyl group directly attached to a trivalent nitrogen atom. The term "dialkylamino" refers to a tertiary amine substituent with two of the same or different alkyl groups directly attached to a trivalent nitrogen atom. The alkyl group is the same as described herein.

In any of the embodiments above, the term "carboxy" refers to the group —C(O)OH. The term "carboxyalkyl" refers to the group —RC(O)OH that is connected to the compound through the alkyl R group. The term "alkoxycarbonyl" refers to the group —OC(O)R, in which R is an alkyl group as described herein.

In any of the embodiments above, the term "amido" refers to the group —C(O)NH$_2$.

In any of the embodiments above, the alkyl, alkoxy, and alkylamino groups can be linear or branched. When an aryl group is substituted with a substituent, e.g., halo, amino, alkyl, hydroxyl, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention.

In any of the embodiments above, whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977). For example, they can be a salt of an alkali metal (e.g., sodium or potassium), alkaline earth metal (e.g., calcium), or ammonium of salt.

The diazeniumdiolated compounds of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

In one aspect of the invention, in formula (Ia) or (Ib), $R^2$ to $R^9$ are each hydrogen. In accordance with another aspect of the invention, in formula (Ia) or (Ib), one of $R^2$ to $R^9$ is alkyl, whereas the remaining substituents of $R^2$ to $R^9$ are hydrogen. In another aspect, $R^1$ is alkyl, aryl alkyl, or aryl, each of which is optionally substituted. In a preferred embodiment, $R^1$ is alkyl, aryl alkyl, or aryl, each of which is optionally substituted and $R^2$ to $R^9$ are each hydrogen.

In a preferred embodiment, a compound of formula (I) or (Ia-c) is $O^2$-(2,4-dinitrophenyl) 1-[(4-ethoxycarbonyl)homopiperazin-1-yl]diazen-1-ium-1,2-diolate ("JS-36-25").

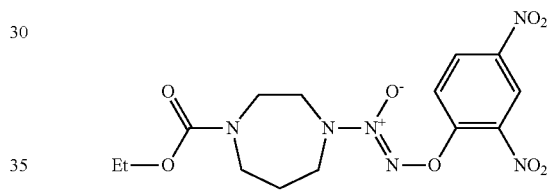

Synthesis of the above compound can be found in Shami et al., *J. Med. Chem.*, 49: 4356-4366 (2006).

Other preferred compounds of formula (I) or (Ia-c) include

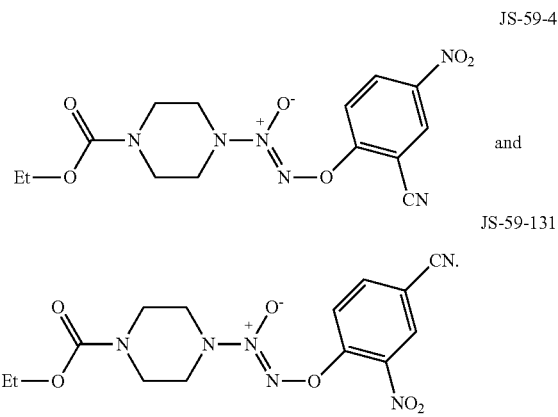

Nitric oxide release from the diazeniumdiolated compounds described herein can be determined/detected using known techniques such as those described in U.S. Pat. Nos. 6,511,991 and 6,379,660; Keefer, et al., "NONOates(1-Substituted Diazen-1-ium-1,2 diolates) as Nitric Oxide Donors: Convenient Nitric Oxide Dosage Forms," *Methods in Enzymology*, 28: 281-293 (1996); Horstmann et al., "Release of nitric oxide from novel diazeniumdiolates monitored by laser magnetic resonance spectroscopy," *Nitric Oxide,* 6(2): 135-41 (2002); and Kitamura et al., "In vivo nitric oxide measurements using a microcoaxial electrode," *Methods Mol. Biol.,* 279: 35-44 (2004), which are incorporated herein by reference. In general, the amount of NO produced can be detected by a chemiluminescence method, electrochemical method, and/or an absorbance method. In addition, nitric oxide assay kits are commercially available.

A diazeniumdiolated compound (e.g., JS-36-25, JS-59-4, JS-59-131) has a prolonged half-life upon treatment with glutathione (GSH) in comparison with that of JS-K (FIG. 1a) suggesting a diminished reactivity of the aromatic ring towards nucleophilic substitution. The prolonged half life may facilitate selective accumulation of the prodrug in cancer tissue by disfavoring reaction with the free glutathione in the bloodstream. It is envisioned that the diminished reactivity of a compound of formula (I) or (Ia-c) towards glutathione and GSH/GST may prove advantageous in the further development of these compounds as anti-cancer agents.

Reactive Oxygen Species (ROS) are derived from the metabolic reduction of molecular oxygen. ROS include the superoxide anion radical ($O_2^-$), singlet oxygen ($^1O_2$), hydrogen peroxide ($H_2O_2$), and the highly reactive hydroxyl radical (OH). These species are highly toxic. ROS normally exist in all aerobic cells in balance with biochemical antioxidants. However, oxidative stress disrupts the critical balance because of excess ROS and/or antioxidant depletion. ROS can cause tissue damage by reacting with lipids in cellular membranes, nucleotides in DNA, sulfhydryl groups in proteins, and crosslinking/fragmentation of ribonucleoproteins. Damage to DNA by ROS is a major cause of cancer. ROS can damage DNA and the division of cells with unpaired or misrepaired damage leads to mutations. The majority of mutations induced by ROS appear to involve modification of guanine, causing G→T transversions. If it relates to critical genes such as oncogenes or tumor suppressor genes, initiation/progression can result. ROS can act at several steps in a multistate carcinogenesis. Cells characterized by increased ROS levels often have depressed levels of antioxidant enzymes.

ROS are also generated when cancer patients are treated with certain chemotherapeutic agents. For example, ROS generation and mitochondrial dysfunction are thought to be involved in the apoptotic response of human H460 NSCLC cancer cells when treated with a proteasome inhibitor, bortezomib.

Peroxiredoxins are antioxidant enzymes effectively scavenging peroxides; they are also recognized as the most efficient peroxynitrite scavengers. The six identified members share a common reactive Cys residue in the N-terminal region, and are capable of serving as a peroxidase and involve thioredoxin and/or glutathione as the electron donor. PRX1 to PRX4 have an additional Cys residue in the conserved C-terminal region, and are cross members as judged by the amino acid sequence similarity. PRX5 also contains an additional Cys in its C-terminal region that is less conserved. On the other hand, PRX6 has only one unique Cys. These PRX family members are distributed in subcellular localization, PRX1, 2, and 6 in cytosol, PRX3 in mitochondria, PRX4 in ER and secretion, PRX5 showing complicated distribution including peroxisome, mitochondria and cytosol, all one or more of which are potential sites of ROS production.

It is surprisingly discovered that protein levels of peroxiredoxin 1 (PRX1) and peroxiredoxin 6 (PRX6) had a correlation with the $IC_{50}$ values for the compound of formula (I) in cancer cell lines. Thus, it is postulated that, in embodiments, low levels of PRX1 and/or PRX6 predispose cancer cells for toxicity via administration of the compound of formula (I) or a salt thereof. For example, the cancer cell PRX6 content in accordance with embodiments of the inventive methods is less than about 30 units, less than about 20 units, or less than about 10 units (e.g., less than about 5 units, less than about 4 units) relative to the PRX6 content of a nonmalignant lung epithelial cell HPL1D which is 100 units. Moreover, for example, in accordance with embodiments of the inventive methods, the cancer cell can have a PRX1 content less than about 100 units (e.g., less than about 90 units, less than about 80 units, less than about 70 units, or less than about 60 units) relative to the PRX1 content of the nonmalignant lung epithelial HPL1D which is 100 units.

A major product of ROS attack in genomic DNA is the premutagenic lesion 7,8-dihydro-8-oxoguanine (8-oxoG), which causes G-to-T transversions. The main defense against the 8-oxoG is the base excision repair (BER) pathway, which in eukaryotes is initiated by the OGG1 protein, a DNA glycosylase that catalyzes the excision of 8-oxodG from DNA. OGG1 is responsible for over 95% of BER activity in mammalian cells. A correlation between OGG1 protein expression levels and $IC_{50}$ values for the compound of formula (I) has been surprisingly discovered. In particular, the compound of formula (I) is less toxic in the cell lines expressing high levels of OGG1 protein. This establishes OGG1 as a potential marker for sensitivity. As a result, in the inventive methods the cancer cell can have an 8-oxo-dG DNA glycosylase (OGG1) content less than about 25 units (e.g., less than about 20 units, less than about 15 units, less than about 10 units, or less than about 5 units) relative to the OGG1 content of the nonmalignant lung epithelial HPL1D which is 100 units.

The amount of PRX1, PRX6, and/or OGG1 in a particular cancer cell can be determined by assays known in the art using, for example, an enzyme-linked immunosorbent assay (ELISA), real-time PCR (RT-PCR), and/or Western blot analysis. For example, commercially available kits can be used (e.g., ELISA for human PRX1 from BioVendor (Candler, N.C.); OGG1 assay kit from Sigma (St. Louis, Mo.)). An example of measuring the expression of PRX6 in a breast cancer cell line using RT-PCR and Western blot analysis can be found in Chang et al., *Breast Cancer Research,* 9(6): R76.

Cancers treatable with the methods described herein include tumors associated with the oral cavity (e.g., the tongue and tissues of the mouth) and pharynx, the digestive system (e.g., the esophagus, stomach, small intestine, colon, rectum, anus, liver, gall bladder, and pancreas), the respiratory system (e.g., the larynx, lung, and bronchus), bones and joints (e.g., bony metastases), soft tissue, the skin (e.g., melanoma and squamous cell carcinoma), breast, the genital system (e.g., the uterine cervix, uterine corpus, ovary, vulva, vagina, prostate, testis, and penis), the urinary system (e.g., the urinary bladder, kidney, renal pelvis, and ureter), the eye and orbit, the brain and nervous system (e.g., glioma), and the endocrine system (e.g., thyroid). The target tissue also can be located in lymphatic or hematopoietic tissues. For example, the tumor can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). The tumor to be treated is not necessarily the primary tumor. Indeed, the tumor can be a metastasis of a primary tumor located in a different tissue or organ.

Specific examples of cancers treatable with the present methods include, without limitation, acute lymphoblastic leukemia, acute myeloid leukemia, adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, chronic lymphocytic, leukemia, chronic myelogenous leukemia, liver cancer, non-small cell lung cancer, small cell lung cancer, Hodgkin's disease, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, gestational trophoblastic tumor, urethral cancer, uterine sarcoma, vaginal cancer, vulvar cancer, and Wilms' tumor.

The cancers that will be treatable by the methods of the present invention include, without limitation, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

In an embodiment of the methods of the invention, the cancer is thyroid cancer, breast cancer, lung cancer, malignant mesothelioma, or non-small cell lung cancer. Preferably, the cancer is non-small cell lung cancer (NSNLC), such as H1703, H1734, H1693, H1568, H1373, H2030, H2023, and H1944. In an embodiment, the NSCLC cell can be an H1703, H1734, or H1693 cell line, which have the following characteristics:

| Cell line | ROS | PRX1 | PRX6 | OGG1 |
|---|---|---|---|---|
| H1703 | 22.0 | 65.8 | 3.3 | 14 |
| H1734 | 18.4 | 108.6 | 2.0 | 103 |
| H1693 | 15.1 | 75.8 | 2.7 | 0.5 |

Preferably, the NSCLC cell is an H1703 or H1693 cell line. These NSCLC cell lines can be distinguished from other lung cancer cell lines, which have one or more biomarkers outside of the desirable range. For example:

| Cell line | ROS | PRX1 | PRX6 | OGG1 |
|---|---|---|---|---|
| H441 | 14.7 | 104.9 | 24.2 | 28 |
| A549 | 2.3 | 174.2 | 12.0 | 260 |
| H1395 | 8.2 | 56.2 | 28.8 | 106 |
| H838 | 6.9 | 79.5 | 86.2 | 204 |

Differential NSCLC cells' responsiveness to the drug appears to be related to the cancer cells' endogenous level of reactive oxygen species (ROS). The level of endogenous ROS correlates significantly with the drug toxicity measured as $IC_{50}$ values. Therefore, it is envisioned that a compound of formula (I), (Ia), (Ib), (Ic), or a salt thereof will have a synergistic effect with therapeutics acting through generation of ROS.

In certain embodiments, the compound of formula (I), (Ia), (Ib), (Ic), or a salt thereof can be co-administered with a chemotherapeutic agent that produces reactive oxygen species (ROS) in the cancer cell. In this regard, the present invention is directed a pharmaceutical composition comprising a pharmaceutically acceptable carrier and a combination of the compound of formula (I), (Ia), (Ib), (Ic), or a salt thereof and a chemotherapeutic agent that produces reactive oxygen species (ROS) in the cancer cell. The cancer cell is the same as described herein.

Examples of chemotherapeutic agents that may produce ROS include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vincristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

In a preferred embodiment, the chemotherapeutic agent that produces ROS is bortezomib or doxorubicin.

The compound of formula (I), (Ia), (Ib), or salt thereof can be administered with a poly ADP ribose polymerase (PARP) inhibitor. The PARP inhibitor can be any suitable compound that inhibits PARP, such as iniparib, olaparib, ABT-888, and AG014699. Preferably, the PARP inhibitor is olaparib. It is contemplated that because certain compounds described herein lead to DNA strand break damage in lung adenocarcinoma cells, a compounds of formula (I), (Ia), (Ib), and (Ic), or a salt thereof have a synergistic cytotoxic effect in combination with a PARP inhibitor. For example, treatment of lung adenocarinoma cells (e.g., cell line H441) with a combination of JS-59-4 and the PARP inhibitor olaparib led to significantly enhanced antiproliferative activity in comparison to treatment with JS-59-4 alone. See FIG. 2.

Alternatively, the compound of formula (I), (Ia), (Ib), (Ic), or a salt thereof can be administered with a high energy radiation that produces ROS.

In the pharmaceutical compositions described herein, any suitable pharmaceutically acceptable carrier can be used, and such carriers are well known in the art. The choice of carrier will be determined, in part, by the particular site to which the pharmaceutical composition is to be administered and the particular method used to administer the pharmaceutical composition.

Suitable formulations include aqueous and non-aqueous solutions, isotonic sterile solutions, which can contain antioxidants, buffers, bacteriostats, and solutes that render the formulation isotonic with the blood or other bodily fluid of the intended recipient, and aqueous and non-aqueous sterile suspensions that can include suspending agents, solubilizers, thickening agents, stabilizers, and preservatives. In one embodiment, the pharmaceutically acceptable carrier is a liquid that contains a buffer and a salt. The formulation can be presented in unit-dose or multi-dose sealed containers, such as ampoules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. In one embodiment, the pharmaceutically acceptable carrier is a buffered saline solution.

Further carriers include sustained-release preparations, such as semipermeable matrices of solid hydrophobic polymers containing the active agent, which matrices are in the form of shaped articles (e.g., films, liposomes, or microparticles).

The pharmaceutical composition can include carriers, thickeners, diluents, buffers, preservatives, surface active agents and the like. The pharmaceutical compositions can also include one or more additional active ingredients, such as antimicrobial agents, anti-inflammatory agents, anesthetics, and the like.

The pharmaceutical composition comprising the compound of formula (I), (Ia), (Ib), (Ic), or a salt thereof can be formulated for any suitable route of administration, depending on whether local or systemic treatment is desired, and on the area to be treated. The pharmaceutical composition can be formulated for parenteral administration, such as intravenous, intraperitoneal, intramuscular, or intratumoral injection. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

Desirably, the pharmaceutical composition also can be administered orally. Oral compositions can be in the form of powders or granules, suspensions or solutions in water or non-aqueous media, capsules, sachets, or tablets. Thickeners, flavorings, diluents, emulsifiers, dispersing aids, or binders may be desirable.

Suitable carriers and their formulations are further described in A. R. Gennaro, ed., *Remington: The Science and Practice of Pharmacy* (19th ed.), Mack Publishing Company, Easton, Pa. (1995).

The pharmaceutical composition can potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The compound or a pharmaceutical composition comprising at least one compound of formula (I), (Ia), (Ib), (Ic), or a salt thereof can be administered in any suitable manner depending on whether local or systemic treatment is desired, and on the area to be treated. Desirably, the pharmaceutical composition is administered orally, but can be administered parenterally, most preferably by intravenous, intraperitoneal, intramuscular, or intratumoral injection. By the term "injecting," it is meant that the pharmaceutical composition is forcefully introduced into the target tissue. Although more than one route can be used to administer the pharmaceutical composition, a particular route can provide a more immediate and more effective reaction than another route. For regional delivery, the pharmaceutical composition can be administered intraarterially or intravenously, e.g., via the hepatic artery for delivery to the liver or the carotid artery for delivery to the brain.

The compound or a pharmaceutical composition comprising at least one compound of formula (I), (Ia), (Ib), (Ic), or a salt thereof can be administered in or on a device that allows controlled or sustained release of the compound of formula (I), (Ia), (Ib), (Ic), or a salt thereof, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the active agents. The pharmaceutical compositions of the inventive method also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid. Of course, administration of the compound or pharmaceutical composition can be accomplished via any route that efficiently delivers the active agents to the target tissue.

The inventive methods comprise administering an effective amount of a compound of formula (I), (Ia), (Ib), (Ic), or a salt thereof. An "effective amount" means an amount sufficient to show a meaningful benefit in an individual, e.g., promoting at least one aspect of tumor cell cytotoxicity, or treatment, healing, prevention, delay of onset, or amelioration of other relevant medical condition(s) associated with a particular cancer. Preferably, one or more symptoms of the cancer are prevented, reduced, or eliminated subsequent to administration of a compound of formula (I), (Ia), (Ib), (Ic), or a salt thereof, thereby effectively treating the cancer to at least some degree.

Effective amounts may vary depending upon the biological effect desired in the individual, condition to be treated, and/or the specific characteristics of the compound of formula (I), (Ia), (Ib), (Ic), or a salt thereof, and the individual. In this respect, any suitable dose of the compound of formula (I), (Ia), (Ib), (Ic), or a salt thereof can be administered to the patient (e.g., human), according to the type of cancer to be treated. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I), (Ia), (Ib), (Ic), or a salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) or (Ia) comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

For purposes of the present invention, the term "patient" preferably is directed to a mammal. Mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The following examples further illustrate the invention but, of course, should not be construed as in any way limiting its scope.

EXAMPLES

Starting materials were purchased from Aldrich Chemical Co. (Milwaukee, Wis.) unless otherwise indicated. 2,4-Dinitro-5-fluorotoluene is purchased from Oakwood Products, Inc. West Columbia, S.C. NMR spectra were recorded on a Varian UNITY INOVA spectrometer; chemical shifts ($\delta$) are reported in parts per million (ppm) downfield from tetramethylsilane. Ultraviolet (UV) spectra were recorded on an Agilent Model 8453 or a Hewlett-Packard model 8451A diode array spectrophotometer. Elemental analyses were performed by Midwest Microlab (Indianapolis, Ind.). Chromatography is performed on a Biotage SP1 Flash Purification System. Pre-packed silica gel flash chromatography columns were purchased from Silicycle (Quebec City, Canada).

All animals used are cared for and used humanely according to the following policies: The U.S. Public Health Service Policy on Humane Care and Use of Animals (1996); the Guide for the Care and Use of Laboratory Animals (1996); and the U.S. Government Principles for Utilization and Care of Vertebrate Animals Used in Testing, Research, and Training (1985). All NCI-Frederick animal facilities and the animal program are accredited by the Association for Assessment and Accreditation of Laboratory Animal Care International.

Example 1

This example demonstrates the in vitro toxicity of JS-36-25 in an embodiment of the invention.

A compound of formula (I), $O^2$-(2,4-dinitrophenyl) 1-[(4-ethoxycarbonyl)homopiperazin-1-yl]diazen-1-ium-1,2-diolate ("JS-36-25"), is synthesized as previously described in Shami et al., *J. Med. Chem.*, 49:4356-4366 (2006).

Cell culture and drug treatment: Cell lines derived from human non-small cell lung cancers are obtained from the American Type Culture Collection and are designated by their NCI numbers. Cells are cultured in RPMI 1640 medium (Invitrogen Life Technologies, Carlsbad, Calif.) supplemented with 10% fetal calf serum (Gemini Bioproducts, Sacramento, Calif.), glutamine and penicillin/streptomycin. Cells are seeded at the density of $2\times10^5$/ml and allowed to attach for 24 hours before drug treatment is started. The compounds are prepared as 10 mM stock solutions in dimethylsulfoxide (DMSO) and diluted to desired concentration with phosphate-buffered saline (PBS) before adding to the culture medium. The final concentration of DMSO in the culture medium do not exceed 0.1%. Protein content of cell lysates is determined with a BCA Protein Assay kit (Pierce Biotechnology, Inc., Rockford, Ill.). All assays are carried out on a minimum of three different cultured cell preparations.

JS-36-25 is toxic to non-small cell lung carcinoma (NSCLC) cells. The drug induced extensive cell death in eight lung adenocarcinoma cell lines with $IC_{50}$ values ranging from 0.4 to 5 µM (FIG. 1B).

Immunoblotting: For protein immunoblotting the cells are harvested in lysis buffer (25 mM Hepes buffer containing 150 mM NaCl, 10 mM $MgCl_2$, 1% Nonidet P40, 0.25% sodium deoxycholate, 10% glycerol, 2.5 mM EDTA, supplemented with Complete proteinase inhibitors cocktail (Behringer). Cell extracts are resolved by SDS-polyacrylamide gel electrophoresis (4-12% Bis-Tris gels or 3-8% Tris-acetate gels, Invitrogen Life Technologies, Carlsbad, Calif.) then immunoblotted to PVDF membrane (Invitrogen). Antibodies to phospho-ATM, Phospho-ATR, cleaved caspases 3 and 7, phospho-SAPK/JNK and SAPK/JNK, phospho-ATF2, phospho-p38 and p38, phospho-c-jun and c-jun, and PARP are purchased from Cell Signaling Technology (Danvers, Mass.). Anti-ATF3 polyclonal antibodies are from Santa Cruz Biotechnology (Santa Cruz, Calif.).

Determination of Reactive Oxygen/Nitrogen Species Generation: Intracellular level of reactive oxygen species is quantified by the oxidation of the ROS/RNS sensitive (Halliwell et al., *Br J Pharmacol.*, 142, (2), 231-55 (2004)), fluorophore 5,6-chloromethyl-2',7'-dichlorodihydrofluorescein diacetate (CM-$H_2$DCF-DA) (Invitrogen, Molecular Probes). Cells are loaded with 5 µM CM-$H_2$DCF-DA in Hanks' balanced salt solution (HBSS) at 37° C. and 5% $CO_2$. After 30 min of incubation the probe is removed, cells are rinsed with HBSS and treated with the compound in HBSS for the time indicated at the figure legends. The 2',7'-dichlorofluorescein (DCF) fluorescence is measured at excitation 488 nm and emission at 530 nm. All experiments are performed three times, each time in triplicate.

The effectiveness of JS-36-25 in NSCLC cells correlates significantly with intracellular ROS levels, measured as the oxidation of the ROS/RNS sensitive fluorophore 5,6-chloromethyl-2',7'-dichlorodihydrofluorescein diacetate (CM-$H_2$DCF-DA). DCF fluorescence correlates negatively with $IC_{50}$ values obtained for the compound of formula (I) (r=−0.76, P=0.037) (FIG. 1C), indicating that cells with higher endogenous ROS are more susceptible for the compound of formula (I) toxicity.

The immediate effect of JS-36-25 treatment is ATM/ATR phosphorylation. Serine 1981 site of ATM and Serine 428 site of ATR are phosphorylated in less than 30 minutes after addition of the drug (FIG. 3A). The downstream effector—checkpoint kinase Chk2 is also activated. It is theorized that ATM/ATR activation could be the result of DNA damage recognition and activation of immediate response pathways.

To investigate signal transduction mechanisms that might be responsible for the cytotoxic effects of JS-36-25, stress kinases SAPK/JNK and p38 that may promote apoptosis when activated is examined. Treatment of H1703 cells with 1 µM JS-36-25 activated SAPK/JNK within less than 30 minutes (FIG. 3B). Activated JNK phosphorylates the proto-oncogene c-jun, which forms both homodimers and heterodimers with c-fos, leading to the activation of the AP-1 transcription factor. The JNK signaling pathway plays major roles in inflammatory responses and apoptosis. The phosphorylation of SAPK/JNK downstream substrates, ATF2 and c-jun, is studied. Phosphorylation of both ATF2 and c-jun increases with similar kinetics as is observed with SAPK/JNK (FIG. 3B). As a loading control, membranes are reprobed against a SAPK/JNK antibody. No variation in the amount of total SAPK/JNK protein is detected. Free radicals and oxidant species can inactivate specific JNK phosphatases and activate upstream signaling molecules in the JNK signaling pathway (Martindale et al., *J Cell Physiol.*, 192(1): 1-15 (2002)). JNK activation in response to peroxynitrite has been reported in a variety of cell types in vitro, including bronchial and alveolar lung cells (Nabeyrat et al., *Am J Physiol Lung Cell Mol Physiol.*, 284(6): L1112-20 (2003); Shrivastava, *Mol Cell Biol.*, 24(15): 6763-72 (2004)). Peroxynitrite-mediated JNK activation has been associated with apoptotic cell death in murine alveolar C10 cells (Shrivastava, *Mol Cell Biol.*, 24(15): 6763-72 (2004)).

p38MAPK is an important member of the MAPK superfamily and is activated in response to various cell stresses, including DNA damage (Johnson et al., *Science*, 298(5600): 1911-2 (2002)). Activation of the p38 pathway can induce a number of cellular responses including necrosis and apoptosis. In H1703 lung cancer cells treated with 1 µM of JS-36-25, phosphorylation of p38MAPK is observed with kinetics similar to that of SAPK/JNK activation. Total amounts of p38 protein do not change (FIG. 3B).

ROS scavenger Tiron significantly reduces both SAPK/JNK and p38 phosphorylation, implicating pre-existing oxidative stress in activation of both stress pathways by JS-36-25. The cells are pre-treated for 1 hour with 10 mM Tiron, followed by 30 minutes incubation with 1 µM of JS-36-25. In the Tiron-treated cells phosphorylation of both SAPK/JNK and p38 by JS-36-25 is diminished in comparison with JS-36-25-only treated cells (FIG. 3C).

ATF-3 has been shown to be a downstream regulator of the JNK-mediated stress kinase signaling pathway (Liang et al., *J. Biol. Chem.*, 271(3): 1695-701 (1996)). Accumulating evidence suggests that ATF3 plays a significant role in apoptosis. When over-expressed, ATF3 induced apoptosis in ovarian cancer cells and sensitized HeLa cells to chemotherapy (Mashima et al., *J. Cell. Physiol.*, 188(3): 352-8 (2001)). ATF3 is also shown to play a role in beta-cells apoptosis (Hartman et al., *Mol. Cell. Biol.*, 24(13): 5721-32 (2004)). Induction of ATF3 often correlates with cellular damage, suggesting an important role during the cellular stress response. Herein, ATF-3 protein expression is induced by JS-36-25 less than 1 hour after the treatment is initiated (FIG. 2D).

Treatment with JS-36-25 causes membrane blebbing, which is recognized as a hallmark of apoptosis. These membrane blebs form earlier than 60 min of exposure to 1 µM of JS-36-25 (FIG. 4A). It has been shown that in some cell systems this precedes mitochondrial cytochrome c release and caspase-3 activation (Maeno et al., *Proc. Natl. Acad. Sci. USA*, 97(17): 9487-92 (2000); Okada et al., *Comp. Biochem. Physiol. A Mol. Integr. Physiol.*, 130(3): 377-383 (2001)). Molecular mechanisms behind apoptotic blebbing are not yet clear. In HUVE cells, CHO cells and also in HeLa cells stimulated with $H_2O_2$, apoptotic bleb formation requires activation of the p38MAPK, with the actin-polymerization promoter HSP27 as its likely downstream effector (Huot et al., *J. Cell. Biol.*, 143(5): 1361-73 (1998); Deschesnes et al., *Mol Biol Cell*, 12(6): 1569-82 (2001)). p38MAPK activation is observed in less than 30 minutes after exposure to 1 µM of JS-36-25.

JS-36-25-induced apoptosis is also confirmed by caspase 3 and 7 activation and PARP cleavage (FIG. 4B).

Taken together, JS-36-25 treatment causes activation of several pathways leading to oxidative/nitrosative stress-induced apoptosis: (i) activation of the mitochondrial pathway, leading to mitochondrial dysfunction, cytochrome c release, and activation of downstream caspases; (ii) activation of the proapoptotic MAPK (JNK and p38); and (iii) ROS/RNS-mediated DNA damage leading to activation of ATM/ATR pathway.

Intracellular Nitric Oxide Release: The intracellular level of nitric oxide after treatment with JS-36-25 is quantified using the NO-sensitive fluorophore 4-amino-5-methylamino-2',7'-difluorofluorescein diacetate (DAF-FM diacetate) (Invitrogen). Cells are loaded with 2.5 µM DAF-FM diacetate in HBSS at 37° C. and 5% $CO_2$. After 30 min of incubation the cells are rinsed with HBSS to remove excess of probe and JS-36-25 in HBSS is added to the cells as indicated on the graph final concentration. After 30 min incubation, the fluorescence of the benzotriazole derivative formed on DAF-FM's reaction with aerobic NO is analyzed using a Perkin Elmer LS50B luminescence spectrometer with the excitation source at 495 nm and emission at 515 nm.

Example 2

This example demonstrates the in vivo toxicity of JS-36-25 in an embodiment of the invention.

All animals used in this research project are cared for and used humanely, in accordance with the procedures outlined in the *Guide for the Care and Use of Laboratory Animals* (National Research Council; 1996; National Academy Press, Washington D.C.). All NCI-Frederick animal facilities and the animal program are accredited by the Association for Assessment and Accreditation of Laboratory Animal Care (AAALAC) International and follow the Public Health Service Policy for the Care and Use of Laboratory Animals.

H1703 cells ($5 \times 10^6$) are injected subcutaneously into a flank of 6-week-old female Ncr nu-nu mice. Tumors are allowed to grow until they reached $2 \times 2 \times 2$ mm. Animals are treated three times a week for three weeks with intravenous injections of either vehicle (2.25% Pluronics in PBS) or JS-36-25 (6 micromoles/kg). Tumors are harvested two hours after the last injection of JS-36-25. Harvested tumors are cut in half and either frozen for processing for proteomic analysis or fixed in 4% paraformaldehyde in PBS, pH 7.4 and processed for immunohistochemistry. Blood is collected by cardiac puncture under isoflurane anesthesia, for testing for cytokines.

JS-36-25 reduces human NSCLC cell growth in the treatment group (13 mice) when compared with control animals (12 mice) treated with vehicle only (FIG. 5A). Most of JS-36-25-treated animals have small tumors well controlled by the drug; in some cases tumors are significantly reduced, below the size when the drug injections are originated (FIG. 5B). Importantly, the treatment with either vehicle or JS-36-25 does not affect body weight.

Statistical Analysis: Results are presented as averages±SE. Statistical tests are carried out using GraphPad Instat version 3.00 (GraphPad Software, San Diego, Calif.). Pair-wise comparisons include the t test, with the Welch correction or application of the Mann-Whitney test as appropriate. Significance of correlations is assessed by linear regression or the Spearman test as appropriate.

Example 3

This example demonstrates the in vivo toxicity of JS-K in an embodiment of the invention.

JS-K is synthesized as described previously (Saavedra et al., *J. Org. Chem.*, 66: 3090-3098(2001)). Cell lines are obtained from the American Type Culture Collection (Manassas, Va.) and cultured according to the supplier's protocol. For proliferation assays cells are seeded at $2 \times 10^4$ per well in 96-well plates and allowed to adhere for 24 h. JS-K is prepared as 10 mM stock solution in DMSO. Increasing drug concentrations in 10 µL of PBS are added to 100 µL of the culture medium for 48 h. MTT assay (Promega, Madison, Wis.) is performed according to the manufacturer's protocol. Each concentration is represented in six repeats, and the screening is performed as at least two independent experiments. $IC_{50}$ values are calculated using Sigma Plot software (Systat Software, Chicago, Ill.).

H1944 or H1703 cells are injected at $5 \times 10^6$ s.c. into a flank of 7-week-old female athymic NCr-nu/nu mice (Charles River, Wilmington, Mass.). The drug injections are initiated when the tumors reached $2 \times 2 \times 2$ mm (typically 3-4 weeks). JS-K is formulated in Pluronic P123 (P123) (BASF, Florham Park, N.J.) micelles. Animals are treated three times a week for three weeks with i.v. tail vein injections of either vehicle (2.25% P123 in PBS) or JS-K (6 µmol/kg in the vehicle). Tumors are measured using a caliper twice a week, and the tumor volumes are calculated using a formula for ellipsoid volume, $\pi/6 \times L \times W \times H$ (Tomayko and Reynolds, 1989). The non-parametric Mann-Whitney test is utilized for statistical comparisons of tumor volumes at each time point. Body weights are taken before each drug injection. Animals are sacrificed 2 h after the last drug injection. Blood is collected by cardiac puncture under isoflurane anesthesia, for testing for cytokines. Cytokines in serum are measured using a mouse Th1/2 multiplex assay (Meso Scale Discovery, Gaithersburg, Md.), according to the manufacturer's protocol. There were 9-13 mice/group at termination.

JS-K inhibits growth of all NSCLC cell lines with $IC_{50}$ concentrations ranging from 0.33 to 17.64 µM (Table 1). Six cell lines are inhibited by JS-K in the range of 0.33-1.01 µM and are thus as sensitive as leukemia cells (Shami et al., *Mol. Cancer Ther.*, 2: 409-417 (2003); Shami et al., *J. Med. Chem.*, 49: 4356-4366 (2006)) or multiple myeloma cells (Kiziltepe et al., *Blood*, 110: 709-718 (2007)).

TABLE 1

| Designation NCI No./ATCC No. | JS-K $IC_{50}$ (µM) | K-ras | p53 |
| --- | --- | --- | --- |
| H1693/CRL5887 | 0.33 | WT | WT |
| H1734/CRL5891 | 0.36 | c13 TGC | mut c273 high |
| H1568/CRL5876 | 0.40 | WT | WT |
| H1703/CRL5889 | 0.40 | WT | mut c285 |
| H1373/CRL5866 | 0.97 | c12 TGT | mut c47 |
| H441/HTB174 | 1.01 | c12 GTT | mut c158 low |
| H1395/CRL5868 | 3.17 | WT | x |
| H2126/CRL5925 | 4.13 | WT | WT |
| H838/CRL5844 | 5.84 | WT | WT |
| H2122/CRL5985 | 6.09 | c12 TGT | x |
| A549/CCL185 | 7.60 | c12 AGT homozygous | WT |
| H460/HTB177 | 7.61 | c61 CAT | WT |
| H1355/CRL5865 | 7.93 | c13 TGC | mut c285 low |
| H322/CRL5806 | 8.71 | WT | mut c248 high |
| H1792/CRL5895 | 9.08 | c12 TGT | mut, splice |
| H2023/CRL5912 | 11.55 | WT | WT |
| H2030/CRL5914 | 14.74 | c12 TGT | WT |
| H1944/CRL5907 | 17.64 | c13 GAC | WT |

$IC_{50}$ values are obtained from 10 concentrations over the range 50 nM to 50 µM, with six replicates for each cell line.
WT = wild type;
c = codon with mutation;
x = not reported Sensitive H1703 cells and resistant H1944 cells are chosen for assessment of activity of JS-K in vivo against xenografted tumor cells in athymic mice. These cell lines have very similar doubling times. JS-K significantly reduces growth of both H1703 and H1944 human NSCLC cells when compared with cells in control animals treated with vehicle only. The growth inhibition is much more pronounced for H1703 xenografts than for H1944 cells, as predicted from the cell culture results (Table 1), although H1944 cells growth in vivo is also significantly inhibited (FIG. 6B). Importantly, the treatment with either vehicle or JS-K did not affect body weight. Serum samples collected from the animals at termination are tested for levels of cytokines; there are no significant differences in levels of IL-1β, IL-2, IL-4, IL-5, IL-10, IL-12t, IFNγ or TNFα between the JS-K-treated and control groups.

Intracellular level of reactive oxygen/nitrogen species is quantified by the oxidation of the ROS/RNS-sensitive fluorophore 5-(and-6)-chloromethyl-2',7'-dichlorodihydrofluorescein diacetate (CM-$H_2$DCF-DA) (Invitrogen, Carlsbad, Calif.). Cells growing on 6-well plates ($6\times10^5$/well) are loaded with 5 µM CM-$H_2$DCF-DA in Hanks' balanced salt solution (HBSS) at 37° C. and 5% $CO_2$. After 30 min of incubation, HBSS containing the probe is removed, cells are rinsed with HBSS and 3 mL of fresh HBSS is added to each well followed by addition of JS-K or DMSO as a control. After 30 min or 60 min the cells are collected by scraping in HBSS and 2',7'-dichlorofluorescein (DCF) fluorescence is measured using a Perkin Elmer LS50B luminescence spectrometer with the excitation source at 488 nm and emission at 530 nm.

The cell lines had previously been characterized with regard to levels of reactive oxygen species (ROS) (Romanowska et al., *Free Radical Biol. Med.*, 43:1145-1155 (2007)). Inspection of the assembled data suggests that JS-K is most effective against cell lines characterized by high levels of ROS, as detected by the oxidation-sensitive fluorophore, 5-(and 6)-chloromethyl-2',7'-dichlorodihydrofluorescein diacetate (DCF). There is a strong and statistically significant correlation between endogenous ROS/RNS (DCF fluorescence) and JS-K toxicity, measured as $IC_{50}$ values (P=0.0004, r=−0.75).

The intracellular level of nitric oxide after JS-K treatment is quantified using the NO-sensitive fluorophore 4-amino-5-methylamino-2',7'difluorofluorescein diacetate (DAF-FM diacetate; Invitrogen, Carlsbad, Calif.). Cells growing on 6-well plates are loaded with 2.5 µM DAF-FM diacetate in HBSS at 37° C. and 5% $CO_2$. After 30 min of incubation the cells are rinsed with HBSS to remove excess probe, and JS-K in fresh HBSS is added to the cells at 1 µM final concentration. After 30 or 60 min incubation the fluorescence of the benzotriazole derivative formed on DAF-FM's reaction with aerobic NO is analyzed using a Perkin Elmer LS50B luminescence spectrometer with the excitation source at 495 nm and emission at 515 nm. All experiments are performed at least three times, each time in triplicate.

An increase in intracellular NO is observed up to 60 min after treatment with the NO-specific reagent 4-amino-5-methylamino-2',7'-difluorofluorescein-diacetate (DAF-FM), and occurred in both the sensitive H1703 and the resistant H1944 cell lines. There is also an increase in DCF-reactive material over this time frame in H1703 cells, but not H1944 cells, suggesting that pre-existing high levels of ROS/RNS are required for generation of additional ROS/RNS.

Mitochondrial and cytosolic fractions are prepared by subcellular fractionation. The cells ($20\times10^6$) are collected with trypsin, rinsed with cold PBS and resuspended in 400 µL of hypotonic buffer (10 mM Tris-HCl, pH 7.5 containing 10 mM NaCl, 1.5 mM $MgCl_2$, 1 mM PMSF and Complete protease inhibitors cocktail (Roche, Indianapolis, Ind.)). Cells are incubated on ice for 10 min and homogenized using a Dounce homogenizer with a B pestle. A volume of 500 µL of mitochondrial buffer (12.5 mM Tris-HCl, pH 7.5 containing 525 mM mannitol, 175 mM sucrose, 2.5 mM EDTA and protease inhibitors) is added to the resulting homogenate, and the mixture is centrifuged twice at 1,300 g for 5 min at 4° C. The resulting supernatant is centrifuged at 10,000 g for 10 min at 4° C. The supernatant (cytosolic fraction) is collected. The pellet (mitochondrial fraction) is resuspended in hypotonic buffer containing 0.5% Triton X-100 and rotated for 30 min at 4° C.

For immunoprecipitation, 300 µg of the cell lysate is incubated on the rotator overnight at 4° C. with 2 µg of anti-nitrotyrosine mAb and 30 µL of protein G agarose. After washing three times with lysis buffer, the beads are suspended in 30 µL of 2×NuPAGE (Invitrogen, Carlsbad, Calif.) loading buffer and heated for 10 min at 95° C. Immunoprecipated material is resolved on SDS-PAGE followed by immunoblotting with anti-MnSOD antibody.

An increase in mitochondrial superoxide generation in the cells is observed. An increase in nitrotyrosine level in MnSOD is detected by immunoprecipitation in H1703 cells after 1 h with JS-K. Involvement of superoxide is also shown using a superoxide scavenger Tiron, which has a protective effect against JS-K toxicity in the H1703 cell line.

For cytochrome c release, H1703 cells are seeded at $2\times10^6$ onto 10-cm Petri dishes and allowed to grow for 24 h. JS-K is added to the medium to a final concentration 1 or 10 µM. Cells are rinsed three times with ice-cold PBS and digitonin [200 µL of 190 µg/mL in lysis buffer (PBS containing 75 mM KCl, 250 mM sucrose and Complete protease inhibitors cocktail (Roche)] is added for 10 min on ice. Cells are then scraped gently and centrifuged 10 min at 12,000 g at 4° C. The supernatant (cytosolic fraction) is removed and the remaining pellet (mitochondrial fraction) is resuspended in 100 µL of lysis buffer (25 mM Hepes buffer containing 150 mM NaCl, 10 mM $MgCl_2$, 1% Nonidet P40, 0.25% sodium deoxycholate, 10% glycerol, 2.5 mM EDTA, and Complete protease inhibitors cocktail) and allowed to incubate for 30 min.

Western blot analysis is performed as previously described (Romanowska et al., *Free Radical Biol. Med.*, 43:1145-1155 (2007)). Primary antibodies for caspases 3, 7, PARP and cleaved PARP, Bax, cytochrome c (Cell Signaling Technology, Danvers, Mass.), peroxiredoxins 1-6 (LabFrontier, Seoul, Korea), and nitrotyrosine and MnSOD (Millipore, Billerica, Mass.) are used.

Mitochondrial superoxide level is measured using Mito-SOX fluorescent dye (Invitrogen, Carlsbad, Calif.), according to the manufacturer's protocol. Rotenone (10 µM) is used as a positive control.

H1703 or H1944 cells are plated in 6-well plates at $6\times10^5$ per well. Cells are treated with JS-K for 1 h at 1 µM (H1703) or 10 µM (H1944). After treatment, cells are washed with PBS, scraped into PBS and collected by centrifugation at 800 g for 10 min. The pellets are resuspended in 80 µL of 10 mM HCl and lysed by two successive rounds of freeze and thawing. Twenty µL of a 5% 5-sulfosalicylic acid solution is added to the lysate. The precipitate is removed by centrifugation at 8,000 g for 10 min, and the supernatant is analyzed for total glutathione content using total glutathione quantification kit (Dojindo, Rockville, Md.) according to the manufacturer's protocol. To measure GSSG concentration, cells are treated and lysed in accordance with the procedure above. The lysate is then neutralized with 0.1 M NaOH and treated with 4-vinylpyridine at a final concentration of 50 mM for 30 min.

H1703 cells are seeded on 24-well plates at $2\times10^5$/well and allowed to grow for 24 h. The cells are then treated with either vehicle (DMSO) or 1-10 µM JS-K and incubated at 37° C., 5% $CO_2$ for 30 min. The JC-1 Mitochondrial Membrane Potential Assay Kit (Cayman Chemical, Ann Arbor, Mich.) is used according to the manufacturer's protocol. The alkaline comet assay is performed as described (Romanowska et al., *Free Radical Biol. Med.*, 43: 1145-1155 (2007)).

A decrease in reduced glutathione (GSH) level and increase in its oxidized (GSSG) form are observed (Table 2). In addition to indirect effects mediated via mitochondrial actions, JS-K may have a direct depleting effect on GSH. JS-K treatment reduced levels of GSH and increased levels of glutathione disulfide (GSSG) in the resistant cell line H1944 as well (Table 2). Untreated H1703 cells have more GSH than H1944 cells.

TABLE 2

|  |  | GSH μmol/mg protein | GSSG μmol/mg protein | $\dfrac{GSH}{GSSG}$ |
|---|---|---|---|---|
| H1703 | DMSO | 1.55 | 0.028 | 55.4 |
|  | JS-K (1 μM) | 1.27 | 0.042 | 30.2 |
| H1944 | DMSO | 0.25 | 0.008 | 31.3 |
|  | JS-K (10 μM) | 0.13 | 0.014 | 9.3 |

Example 4

This example demonstrates the synthesis of $O^2$-(2,4-dinitrophenyl-5-methyl) 1-[(4-ethoxycarbonyl)piperazin-1-yl]diazen-1-ium-1,2-diolate (JS-55-111) (6) in an embodiment of the invention (Scheme 1).

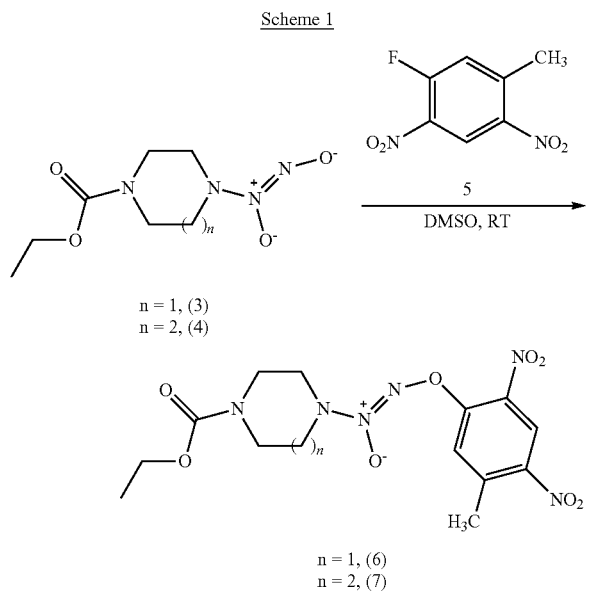

Scheme 1 n = 1, (3)
n = 2, (4)

n = 1, (6)
n = 2, (7)

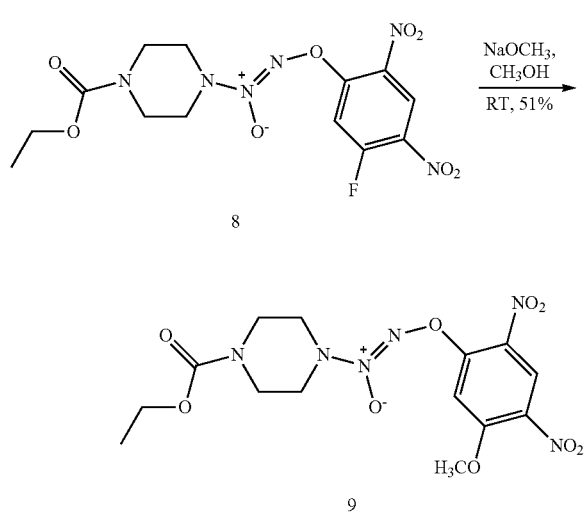

8

9

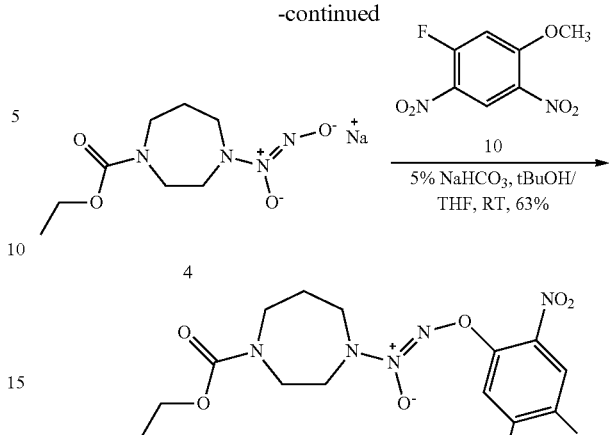

10

11

A solution 3 (543 mg, 2.5 mmol) in 10 mL of DMSO is stirred at room temperature. A solution of 5 (500 mg, 2.5 mmol) in 5 mL of DMSO is added through a syringe. The solution turned green upon addition and faded to yellow gradually. The solution is stirred at room temperature for 72 h, flooded with 25 mL of ice-water, and extracted with ether. The organic layer is dried over sodium sulfate and filtered through a layer of anhydrous magnesium sulfate. Evaporation of the solvent gives a yellow solid that is recrystallized from ether-petroleum ether to give of compound 6 (409 mg). The aqueous/DMSO layer is allowed to stand overnight producing an additional 181 mg of product 6 (total yield: 64%). Mp 81-83° C.; UV (ethanol) $\lambda_{max}$ (ε) 252 nm (12.2 mM$^{-1}$ cm$^{-1}$), $\lambda_{max}$ (ε) 290 nm (11.6 mM$^{-1}$ cm$^{-1}$); $^1$NMR (CDCl$_3$) δ 1.29 (t, J=7.0 Hz, 3H), 2.75 (s, 3H), 3.60-3.63 (m, 4H), 3.72-3.75 (m, 4H), 4.19 (q, J=7.0 Hz, 2H) 7.44 (s, 1H), 8.78 (s, 1H), (1.21 and 3.48 ether); $^{13}$C NMR (CDCl$_3$) δ 14.62, 21.61, 42.24, 50.68, 62.08, 120.70, 123.05, 123.85, 141.94, 151.89, 155.01. Anal. (C$_{14}$H$_{18}$N$_6$O$_8$)C, H, N.

Example 5

This example demonstrates the synthesis of $O^2$-(2,4-dinitrophenyl-5-methyl) 1-[(4-ethoxycarbonyl)homopiperazin-1-yl]diazen-1-ium-1,2-diolate (RN-2-45) (7) in an embodiment of the invention (Scheme 1).

To a solution of 4 (254 mg, 1.0 mmol) in 5 mL DMSO is added solution of 5 (200 mg, 1.0 mmol) in 1 mL DMSO at room temperature. After 12 h, the reaction is quenched with ice-water and extracted with ether. The combined organic layer is dried over anhydrous sodium sulfate and solvent is evaporated under reduced pressure. The crude material is purified by flash column chromatography (1:1 hexane/ethyl acetate) to afford product 7 (190 mg, 46%) as a yellow solid. UV (ethanol) $\lambda_{max}$ (ε) 304 nm (17.7 mM$^{-1}$ cm$^{-1}$); $^1$H NMR (DMSO-d$_6$, 70° C.) δ 1.09 (t, J=7.0 Hz, 3H), 1.83-1.89 (m, 2H), 2.62 (s, 3H), 3.40 (t, J=5.8 Hz, 2H), 3.64 (t, J=5.9 Hz, 2H), 3.89 (t, J=5.7 Hz, 2H), 3.95-4.00 (m, 4H), 7.60 (s, 1H), 8.66 (s, 1H); $^{13}$C NMR (DMSO-d$_6$, 70° C.) δ 14.81, 20.88, 25.71, 44.17, 45.66, 50.25, 50.62, 61.25, 120.54, 123.68, 135.03, 142.39, 142.85, 151.90, 155.48. Anal. (C$_{15}$H$_{20}$N$_6$O$_8$) C, H, N.

Example 6

This example demonstrates the synthesis of $O^2$-(2,4-dinitrophenyl-5-methoxy) 1-[(4-ethoxycarbonyl)piperazin-1-yl]diazen-1-ium-1,2-diolate (JS-56-32) (9) in an embodiment of the invention (Scheme 1).

To a solution of 8 (246 mg, 0.612 mmol) in 10 mL of dichloromethane is added 5.4 M sodium methoxide in methanol (0.113 mL, 0.612 mmol). The resulting orange solution fades to a light yellow-orange solution. TLC analysis on silica gel using 10:1 dichloromethane: ethyl acetate indicates that all the staring material reacts within the first 5 minutes of reaction. The solution is diluted with 25 mL of dichloromethane, washed with water, dried over sodium sulfate and filtered through a layer of anhydrous magnesium sulfate and evaporated under vacuum to give 208 mg of a resin. The resin solidified upon trituration with ether and the resulting yellow powder is collected by filtration giving product 10 (128 mg, 51%). Mp 142-144° C.; UV (ethanol) $\lambda_{max}$ ($\epsilon$) 276 nm (10.2 mM$^{-1}$ cm$^{-1}$); $^1$H NMR (CDCl$_3$) $\delta$ 1.29 (t, J=7.0 Hz, 3H) 3.57-3.62 (m, 4H), 3.72-3.75 (m, 4H), 4.09 (2, 3H), 4.19 (q, J=7.0 Hz, 2H) 7.11 (s, 1H), 8.79 (s, 1H); $^{13}$C NMR, (CDCl$_3$) $\delta$ 14.61, 42.20, 50.71, 57.54, 62.10, 101.52, 125.57, 154.21, 157.84, 165.87, 175.96. Anal. ($C_{14}H_{18}N_6O_9$) C, H, N.

Example 7

This example demonstrates the synthesis of $O^2$-(2,4-dinitrophenyl-5-methoxy) 1-[(4-ethoxycarbonyl)homopiperazin-1-yl]diazen-1-ium-1,2-diolate (RN-2-50) (11) in an embodiment of the invention (Scheme 1).

To a solution of 4 (254 mg, 1.0 mmol) in 5% sodium bicarbonate (8 mL) is added solution of 10 (216 mg, 1.0 mmol) in THF/tBuOH (1:1, 8 mL) at room temperature. After 12 h, reaction is diluted with 15 mL ether, and the organic layer is separated. The aqueous layer is extracted with ether (2×10 mL). The combined organic layer is dried over anhydrous sodium sulfate and solvent is evaporated under reduced pressure. The crude material is purified by flash column chromatography (1:1 hexane/ethyl acetate) to afford product 11 (270 mg, 63%) as a yellow solid. UV (ethanol) $\lambda_{max}$ ($\epsilon$) 305 nm (14.1 mM$^{-1}$ cm$^{-1}$); $^1$H NMR (DMSO-d$_6$, 70° C.) $\delta$ 1.09 (t, J=7.00 Hz, 3H), 1.88 (broad, 2H), 3.40 (t, J=6.0 Hz, 2H), 3.65 (t, J=5.4 Hz, 2H), 3.90 (t, J=5.5 Hz, 2H), 3.94-4.01 (m, 4H), 4.06 (s, 3H), 7.29 (s, 1H), 8.68 (s, 1H); $^{13}$C NMR (DMSO-d$_6$, 70° C.) $\delta$ 14.92, 25.54, 44.20, 45.59, 50.13, 50.56, 58.49, 61.28, 120.00, 125.28, 129.30, 133.03, 154.48, 157.90. Anal. ($C_{15}H_{20}N_6O_9$) C, H, N.

Example 8

This example demonstrates a stability study of compound 6, 7, 9, and 11 in an embodiment of the invention.

490 µL of 2.25% Pluronic P123 in PBS is aliquoted into glass HPLC vials and maintained at 50° C. To this solution, 10 µL of 50 mM of compounds 6, 7, 9, and 11 in DMSO is added and maintained at 50° C. for 10 min. A glutathione stock solution (40 mM) is prepared in 0.1 M phosphate buffer pH 7.4. To 800 µL of 0.1 M phosphate buffer in a glass HPLC vial, 100 µL of glutathione stock solution and 100 µL of formulated prodrug are added. The disappearance of the compound is monitored using an Agilent 1100 series HPLC fitted with a C-18 reverse phase column (Phenomenex Luna 250× 4.60 mm) operating at 300 nm and run isocratically with acetonitrile:water (75:25).

The rates of reaction of 1 (JS-K) and its analogues with 4 mM glutathione (GSH) in aqueous pH 7.4 phosphate buffered saline at 37° C. are determined (Table 3). The results show that substituting phenyl ring with toluyl or anisyl rings significantly increased half-life in the reaction with 4 mM glutathione (Table 3). Substituting piperazine moiety with homopiperazine also resulted in more stable compound 2 (JS-36-25).

TABLE 3

| Compound | t½ (min) Mean (SE) |
|---|---|
| 1 | 15.7 (1.4) |
| 6 | 71.5 (4.3) |
| 9 | 38.6 (2.8) |
| 2 | 22.6 (0.4) |
| 7 | 25.7 (1.0) |
| 11 | 59.6 (4.2) |

Example 9

This example demonstrates a cell culture and proliferation assay for compounds 6, 7, 9, and 11 in an embodiment of the invention.

Cell lines derived from human non-small cell lung cancers are obtained from American Type Culture Collection (ATCC, Manassas, Va.), and are designated by their NCI numbers. Cells are maintained in RPMI 1640 medium (Gibco, Invitrogen, Carlsbad, Calif.), supplemented with 10% fetal calf serum (Gemini Bio-Products, Sacramento, Calif.), 100 U/mL penicillin/streptomycin, and 2 mM glutamine at 37° C. and 5% $CO_2$.

For proliferation assays cells are seeded at $2 \times 10^4$/well in 96-well plates, allowed to adhere for 24 hrs, and then are treated with the drug or DMSO as a control for 48 hours. Final concentration of DMSO did not exceed 0.1%. Compounds are prepared as 10 mM stock solution in dimethyl sulfoxide (Sigma, St. Louis, Mo.). Increasing drug concentrations in 10 µL of phosphate-buffered saline (PBS) are added to 100 µL of the culture medium and incubated at 37° C. for 72 h. The CellTiter 96 non-radioactive cell proliferation assay (MTT assay, Promega, Madison, Wis.), is performed according to the manufacturer's protocol. Each compound concentration is represented in six repeats, and the screening is performed as at least two independent experiments. IC$_{50}$ values are calculated using Sigma Plot software (Systat Software).

Compounds 1 and 2 exhibited very comparable antiproliferative activities against NSCLC cell lines (Table 4).

TABLE 4

| Compound | IC$_{50}$ (µM) | | | | |
|---|---|---|---|---|---|
| | H1703 | H441 | H1373 | H2122 | H1944 |
| 1 | 0.57 | 0.94 | 0.86 | 3.17 | >10 |
| 6 | 0.97 | 1.61 | 1.86 | 7.00 | >10 |
| 9 | 1.57 | 2.50 | 2.10 | 5.78 | >10 |
| 2 | 0.64 | 1.42 | 0.95 | 3.14 | >10 |
| 7 | 1.66 | 2.02 | 3.00 | 10.0 | >10 |
| 11 | 1.82 | 3.15 | 3.08 | 10.0 | >10 |

Example 10

This example demonstrates in vivo administration of compounds 1, 2, and 6 in an embodiment of the invention.

H1703 cells are harvested at 80% confluence, washed with PBS, and suspended in PBS. The cells are injected at $5 \times 10^6$ s.c. into a flank of 7-week-old female athymic NCr-nu/nu mice (Charles River). The drug injections are initiated when the tumors reached at least 2×2×2 mm (typically 4 weeks). Animals are treated three times a week for three weeks with i.v. tail vein injections of either vehicle (2.25% P-123 in PBS) or 1 or 2 (6 micromols/kg in the vehicle) or 6 (8 micromols/kg). Body weights are taken before each drug injection. Animals are sacrificed two hours after the last drug injection and the tumors are excised and weighed. There are 13-15 mice/group at termination. The non-parametric Mann-Whitney test is utilized for statistical comparisons of tumor weights.

Western blot analysis is performed as previously described (Romanowska et al., *Free Radical Biol. Med.*, 43: 1145-1155 (2007)). Primary antibodies for caspases 3, 7, PARP and cleaved PARP, P-SEK1/MMK4, P-SAPK/JNK and SAPK/JNK, P-ATF2, P-c-jun (Cell Signaling Technology), ATF3 (Santa Cruz Biotechnology) are used. Paraffin-embedded xenograft tumor sections are analyzed for P-SAPK/JNK and ATF3 by immunohistochemistry using the antibody against P-SAPK/JNK (Cell Signaling, #4668) or ATF3 (Santa Cruz, c-188). The staining intensity of the cells is categorized as negative (−), very weak (−/+), weak (+), moderate (++), or strong (+++), For flow cytometric analysis (fluorescence-activated cell sorter [FACS]), cells are trypsinized, washed twice with ice-cold PBS, resuspended in PBS, fixed by the addition of absolute ethanol to a final concentration of 70%, and held at −20° C. Two hours before the FACS analysis, the cells are washed with PBS and resuspended in PBS, and the cell nuclei are stained in the dark with 100 μg/mL propidium iodide (Sigma, St. Louis, Mo.) containing 125 U/mL RNase. Ten thousand stained nuclei are analyzed on a BD FACSCanto II using BD FACS DIVA software from Becton Dickinson Immunocytometry Systems, San Jose, Calif. The cell cycle analysis is done using ModFit LT from Verity House Software, Inc, Topsham, Me.

Treatment with 1 or 2 significantly reduced growth of H1703 human NSCLC cells when compared with cells in control animals treated with vehicle only. Treatment with 1 led to 49% reduction of the tumor weights (P<0.05). Treatment with 2 resulted in 63% reduction of the tumor weights (P<0.01). Regardless of the higher dose, treatment with 6 did not result in reduction in H1703 tumor growth in vivo. Importantly, the treatment with either vehicle or diazeniumdiolate-based drugs did not affect body weights.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating non-small cell lung cancer in a patient comprising administering to the patient an effective amount of a diazeniumdiolated ($N_2O_2$-containing) compound of formula (Ia) or a pharmaceutically acceptable salt thereof,

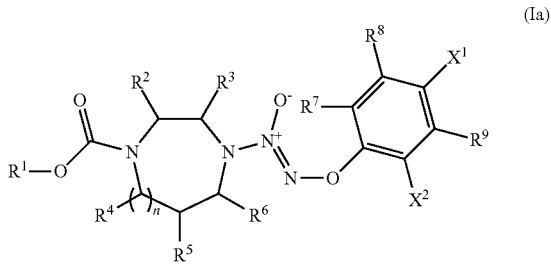

wherein
  $R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and
  $R^2$, $R^3$, $R^4$, $R^5$, $R^6$, $R^7$, $R^8$, and $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;
  $X^1$ and $X^2$ are independently nitro or cyano;
  n is 0, and
  wherein the non-small cell lung cancer cell has an elevated level of reactive oxygen species (ROS) and/or a decreased level of one or more of PRX1, PRX6, and OGG1, compared to a normal cell of the same tissue or tissue type.

2. The method of claim 1, wherein $R^1$ is alkyl that is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino.

3. The method of claim 1, wherein $R^2$, $R^3$, $R^5$, and $R^6$ are each H.

4. The method of claim 1, wherein $R^7$ and $R^9$ are each H; and $R^8$ is H, alkyl, or alkoxy.

5. The method of claim 1, wherein the compound of formula (Ia) is

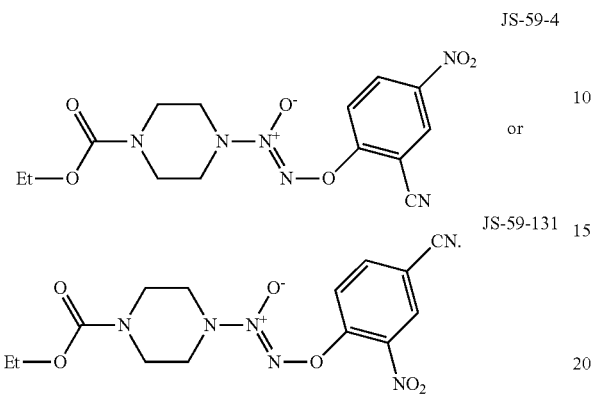

6. The method of claim 1, wherein the non-small cell lung cancer cell has an elevated level of reactive oxygen species (ROS) compared to a normal cell of the same tissue or tissue type.

7. The method of claim 1, wherein the non-small cell lung cancer cell has a decreased level of one or more of PRX1, PRX6, and OGG1 compared to a normal cell of the same tissue or tissue type.

8. The method of claim 1, wherein the non-small cell lung cancer cell has a peroxiredoxin 6 (PRX6) content less than about 10 units relative to the PRX6 content of a nonmalignant lung epithelial cell HPL1D which is 100 units.

9. The method of claim 8, wherein the non-small cell lung cancer cell has a PRX6 content less than about 5 units relative to the PRX6 content of a nonmalignant lung epithelial cell HPL1D which is 100 units.

10. The method of claim 8, wherein the non-small cell lung cancer cell further has a peroxiredoxin 1 (PRX1) content less than about 100 units relative to the PRX1 content of the nonmalignant lung epithelial HPL1D which is 100 units.

11. The method of claim 1, wherein the non-small cell lung cancer cell has an 8-oxo-dG DNA glycosylase (OGG1) content less than about 25 units relative to the OGG1 content of the nonmalignant lung epithelial HPL1D which is 100 units.

12. The method of claim 1, wherein the cancer is a non-small cell lung cancer (NSCLC) cell selected on the basis of quantification parameters established from studies of H1703, H1734, H1693, H1568, H1373, H2030, H2023, and H1944 cell lines.

13. The method of claim 12, wherein the quantification parameters include one or more of PRX1, PRX6, and OGG1 obtained from biopsies of the NSCLC tissue.

14. The method of claim 1, wherein the compound or a salt thereof is co-administered with a chemotherapeutic agent that produces reactive oxygen species (ROS) in the cancer cell or with a high energy radiation,
wherein the chemotherapeutic agent is selected from the group consisting of cisplatin, carboplatin, oxaliplatin, cyclophosphamide, ifosfamide, chlorambucil, nitrogen mustard, thiotepa, melphalan, busulfan, procarbazine, streptozocin, temozolomide, dacarbazine, bendamustine, daunorubicin, doxorubicin, idarubicin, epirubicin, mitoxantrone, bleomycin, mytomycin C, plicamycin, dactinomycin, paclitaxel, docetaxel, 5-fluorouracil, cytarabine, premetrexed, thioguanine, floxuridine, capecitabine, methotrexate, fludarabine, clofarabine, cladribine, pentostatin, nelarabine, topotecan, irinotecan, azacitidine, decitabine, bortezomib, etoposide, teniposide, hydroxyurea, vincristine, vindesine, vinorelbine, vinblastine, imatinib, dasatinib, nilotinib, sorafenib, sunitinib, rituximab, cetuximab, panetumumab, tositumomab, trastuzumab, alemtuzumab, gemtuzumab ozogamicin, bevacizumab, carmustine, fotemustine, lomustine, L-Asparaginase, hexamethylmelamine, mitotane, thalidomide, lenalidomide, prednisone, dexamethasone, prednisolone, tamoxifen, raloxifene, leuprolide, bicaluatmide, granisetron, flutamide, letrozole, anastrozole, arsenic trioxide, tretinoin, salicylates, aspirin, piroxicam, ibuprofen, indomethacin, naprosyn, diclofenac, tolmetin, ketoprofen, nabumetone, oxaprozin, and any combination thereof.

15. The method of claim 14, wherein the chemotherapeutic agent is bortezomib or doxorubicin.

16. The method of claim 1, wherein the compound or salt is co-administered to the patient with a PARP inhibitor selected from the group consisting of iniparib, olaparib, ABT-888, and AG014699.

17. A method of enhancing chemotherapeutic treatment of cancer with a chemotherapeutic agent that produces reactive oxygen species (ROS) in the cancer cell or radiation treatment of non-small cell lung cancer, the method comprising administering an effective amount of a diazeniumdiolated compound of the formula (Ia):

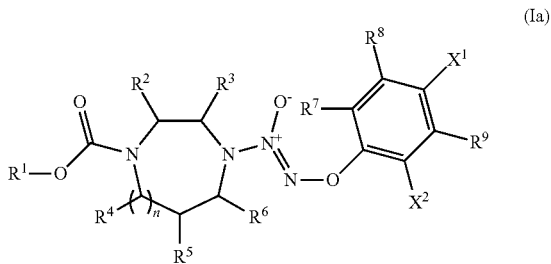

wherein
$R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and
$R^2$, $R^3$, $R^4$, $R^5$, $R^6$, $R^7$, $R^8$, and $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;
$X^1$ and $X^2$ are independently nitro or cyano; and
n is 0;
or a pharmaceutically acceptable salt thereof,
wherein the chemotherapeutic agent is selected from the group consisting of cisplatin, carboplatin, oxaliplatin, cyclophosphamide, ifosfamide, chlorambucil, nitrogen mustard, thiotepa, melphalan, busulfan, procarbazine, streptozocin, temozolomide, dacarbazine, bendamustine, daunorubicin, doxorubicin, idarubicin, epirubicin, mitoxantrone, bleomycin, mytomycin C, plicamycin, dactinomycin, paclitaxel, docetaxel, 5-fluorouracil, cytarabine, premetrexed, thioguanine, floxuridine, capecitabine, methotrexate, fludarabine, clofarabine, cladribine, pentostatin, nelarabine, topotecan, irinotecan, azacitidine, decitabine, bortezomib, etoposide, teniposide, hydroxyurea, vincristine, vindesine, vinorelbine, vinblastine, imatinib, dasatinib, nilotinib, sorafenib, sunitinib, rituximab, cetuximab, panetumumab, tositumomab, trastuzumab, alemtuzumab, gemtuzumab ozogamicin, bevacizumab, carmustine, fotemustine, lomustine, L-Asparaginase, hexamethylmelamine, mitotane, thalidomide, lenalidomide, prednisone, dexamethasone, prednisolone, tamoxifen, raloxifene, leuprolide, bicaluatmide, granisetron, flutamide, letrozole, anastrozole, arsenic trioxide, tretinoin, salicylates, aspirin, piroxicam, ibuprofen, indomethacin, naprosyn, diclofenac, tolmetin, ketoprofen, nabumetone, oxaprozin, and any combination thereof.

18. The method of claim 17, wherein the compound or salt is administered simultaneously with the chemotherapeutic treatment or radiation treatment, sequentially with chemotherapeutic treatment or radiation treatment, or cyclically with chemotherapeutic treatment or radiation treatment.

19. The method of claim 18, wherein the compound or salt is administered prior to the chemotherapeutic treatment or radiation treatment.

20. The method of claim 18, wherein the compound or salt is administered subsequent to the chemotherapeutic treatment or radiation treatment.

21. The method of claim 17, wherein $R^1$ is alkyl that is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino.

22. The method of claim 17, wherein $R^2$, $R^3$, $R^5$, and $R^6$ are each H.

23. The method of claim 17, wherein $R^7$ and $R^9$ are each H; and $R^8$ is H, alkyl, or alkoxy.

24. The method of claim 17, wherein the compound of formula (Ia) is

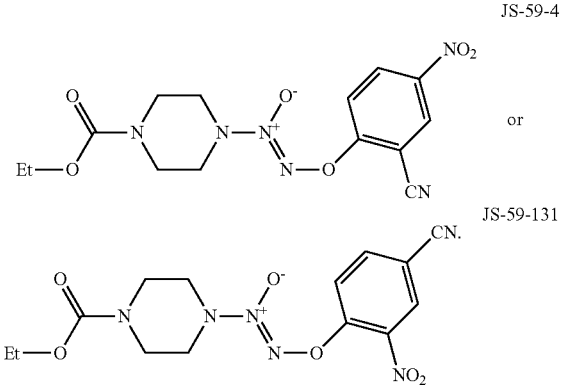

25. A compound of the formula (Ic):

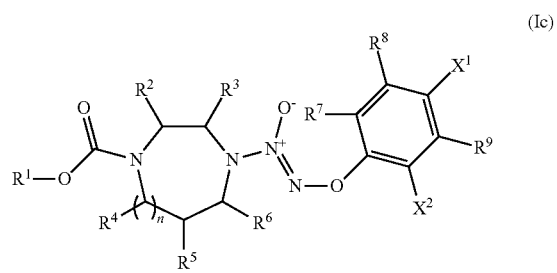

wherein $R^1$ is selected from the group consisting of alkyl, alkenyl, alkynyl, aryl alkyl, aryl, heterocyclic, heteroaryl, and heteroaryl alkyl, each of which is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino; and $R^2$, $R^3$, $R^4$, $R^5$, $R^6$, $R^7$, $R^8$, and $R^9$ are independently selected from the group consisting of H, halo, alkyl, alkenyl, alkynyl, aryl alkyl, aryl, heterocyclic, heteroaryl, heteroaryl alkyl, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino;

$X^1$ and $X^2$ are independently nitro or cyano;

wherein at least one of $X^1$ and $X^2$ is cyano;

n is 0;

or a pharmaceutically acceptable salt thereof.

26. The compound of claim 25, wherein $R^1$ is alkyl that is optionally substituted with a substituent selected from the group consisting of halo, OH, CN, hydroxyalkyl, haloalkyl, aminoalkyl, alkoxy, aryloxy, thioalkoxy, nitro, sulfonato, formyl, acyl, acyloxy, carboxyl, mercapto, alkoxycarbonyl, alkoxycarbonyloxy, amido, amino, alkylamino, and dialkylamino.

27. The compound of claim 25, wherein $R^2$, $R^3$, $R^5$, and $R^6$ are each H.

28. The compound of claim 25, wherein $R^7$ and $R^9$ are each H; and $R^8$ is H, alkyl, or alkoxy.

29. The compound of claim 25, wherein the compound of formula (Ic) is

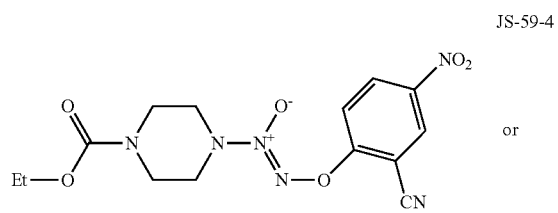

-continued
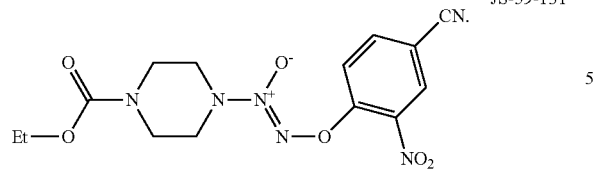
JS-59-131
30. A pharmaceutical composition comprising a compound or salt of claim 25 and a pharmaceutically acceptable carrier.
31. A method of treating non-small cell lung cancer in a patient comprising administering an effective amount of a compound or salt of claim 25 to the patient.
* * * * *